(12) United States Patent
Chang

(10) Patent No.: US 7,858,102 B2
(45) Date of Patent: Dec. 28, 2010

(54) **COMPOSITIONS FOR ELICITING AN IMMUNE RESPONSE AGAINST *MYCOBACTERIUM AVIUM* SUBSPECIES *PARATUBERCULOSIS***

(75) Inventor: Yung-Fu Chang, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 254 days.

(21) Appl. No.: 11/816,365

(22) PCT Filed: Feb. 16, 2006

(86) PCT No.: PCT/US2006/005509

§ 371 (c)(1),
(2), (4) Date: Jun. 4, 2008

(87) PCT Pub. No.: WO2006/089043

PCT Pub. Date: Aug. 24, 2006

(65) Prior Publication Data

US 2010/0034855 A1     Feb. 11, 2010

Related U.S. Application Data

(60) Provisional application No. 60/653,536, filed on Feb. 16, 2005.

(51) Int. Cl.
*A61K 39/04* (2006.01)
*A61K 39/02* (2006.01)
*A61K 39/00* (2006.01)
*A61K 31/70* (2006.01)

(52) U.S. Cl. .............. 424/248.1; 424/234.1; 424/184.1; 514/44; 536/23.7

(58) Field of Classification Search ....................... None
See application file for complete search history.

(56) References Cited

FOREIGN PATENT DOCUMENTS

WO    WO 03/076898 A    9/2003

OTHER PUBLICATIONS

Uzonna et al.; Efficacy of commercial and field-strain *Mycobacterium paratuberculosis* vaccinations with recombinant IL-12 in a bovine experimental infection model; Vaccine, 2003, vol. 21; pp. 3101-3109.
Mullerad et al.; The immunogenicity of *Mycobacterium paratuberculosis* 85B antigen; Med. Microbiol. Immunol., 2002, vol. 190; pp. 179-187.
Shin et al.; Comparative antibody response of five recombinant antigens in related to bacterial shedding levels and development of serological diagnosis based on 35 kDa antigen for *Mycobacterium avium* subsp. *paratuberculosis*; J. Vet. Sci., 2004, vol. 5, No. 2; pp. 111-117.
Dheenadhayalan, et al.; Cloning and Characterization of the Genes Coding for Antigen 85A, 85B and 85C of *Mycobacterium avium* subsp. *paratuberculosis*; DNA Sequence, 2002, vol. 13, No. 5; pp. 287-294.
Velaz-Faircloth, et al.; Protection against *Mycobacterium avium* by DNA Vaccines Expressing Mycobacterial Antigens as Fusion Proteins with Green Fluorescent Protein; Infection and Immunity, Aug. 1999, vol. 67, No. 8; pp. 4243-4250; XP 002491854.
Sechi et al., Immunization with DNA vaccines encoding different mycobacterial antigens elicits a Th1 type immune response in lambs and protects against *Mycobacterium avium* subspecies *paratuberculosis* infection; (Abstract) Vaccine. Jan. 16, 2006;24(3):229-35.
Shin et al.; In Vitro Cellular Immune Responses to Recombinant Antigens of *Mycobacterium avium* subsp. *paratuberculosis*; Infection and Immunity, Aug. 2005, vol. 73, No. 8; pp. 5074-5085.
Körmendy; *Paratuberculosis* vaccine in a large dairy herd; Acta Vet Hung. 1992, vol. 40, No. 3; 1 page.

*Primary Examiner*—S. Devi
(74) *Attorney, Agent, or Firm*—Hodgson Russ LLP

(57) ABSTRACT

The invention provides compositions and method for stimulating an immunological response against *Mycobacterium avium* subspecies *paratuberculosis* (MPT). The compositions comprise at least five recombinant immunogenic components. The immunogenic components can be MPT antigens or DNA polynucleotides encoding MPT antigens, or combinations thereof. MPT antigens used in the invention include MPT 85A, 85B, 85C, 35 kDa, super oxide dismutase (SOD), MptC, MptD and ESAT-6 protein. The method comprises administering the composition to an animal in an amount effective to stimulate an immunological response against MPT bacteria. The method is of benefit to any animal susceptible to MPT infection, but is particularly beneficial for ruminants.

9 Claims, 15 Drawing Sheets

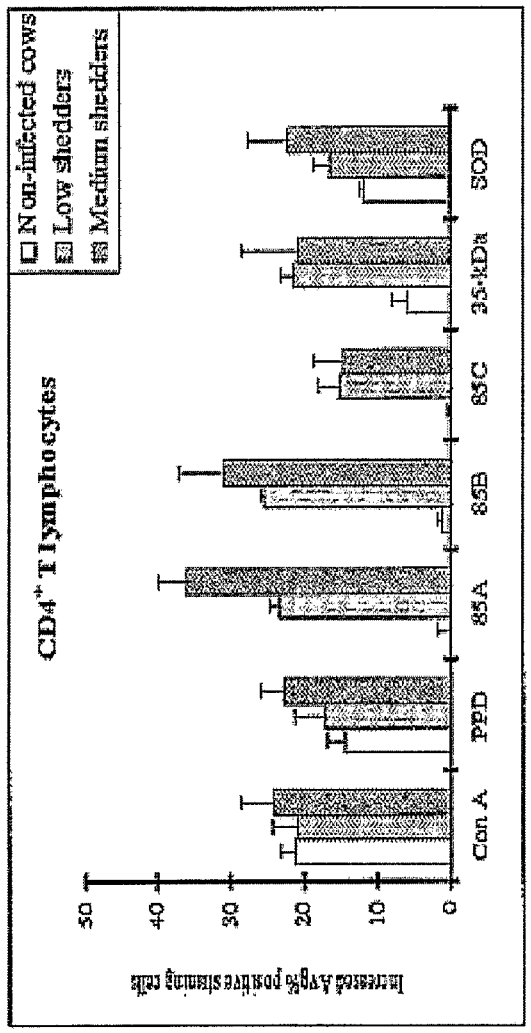
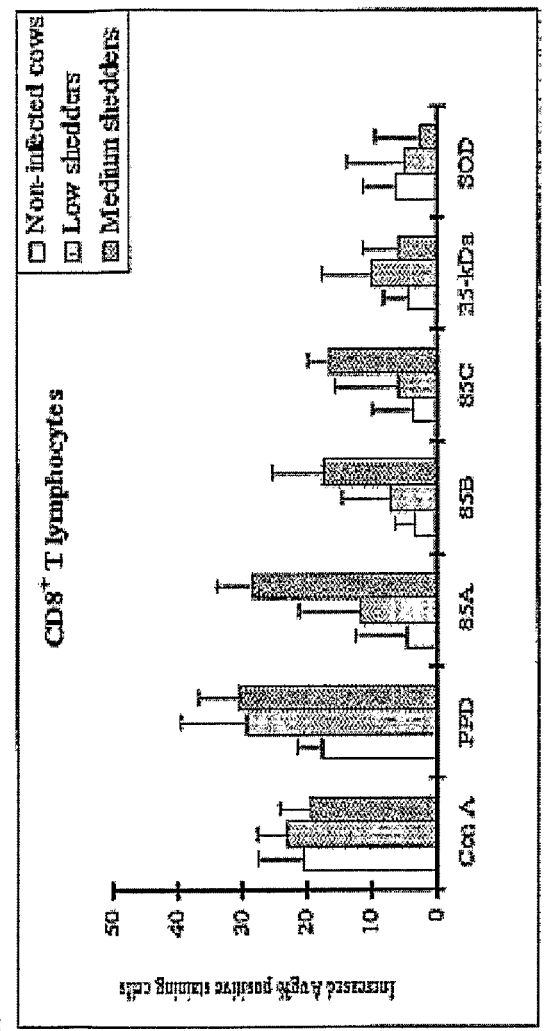
Fig. 4A
Fig. 4B

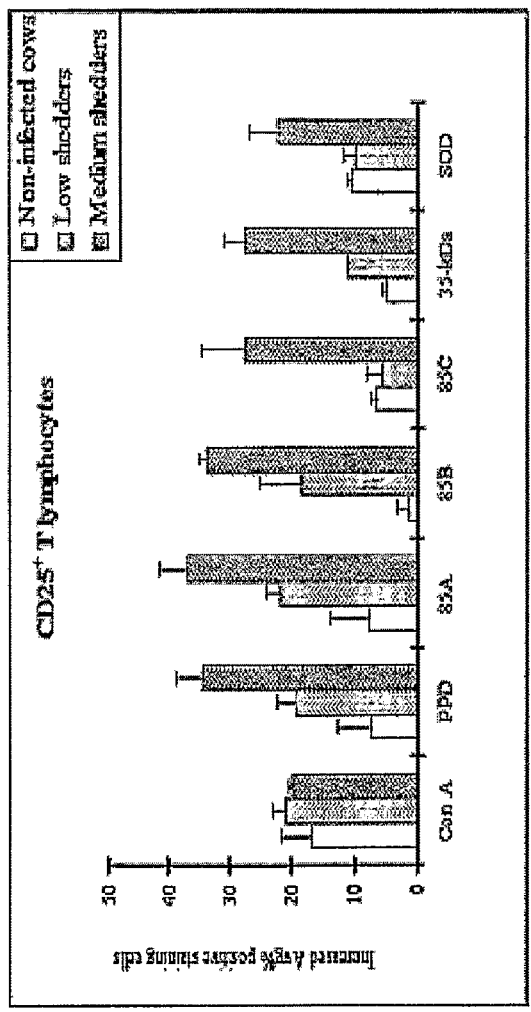
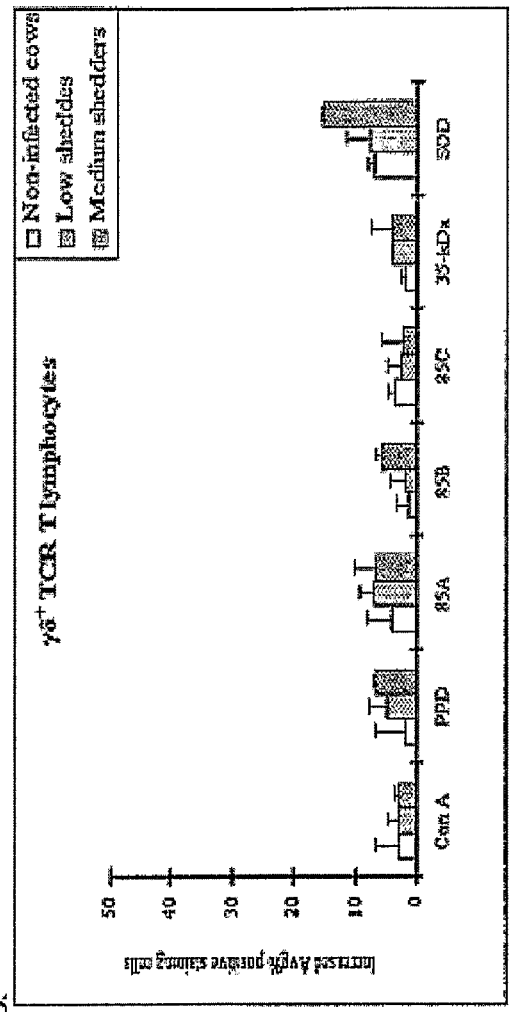
Fig. 4C
Fig. 4D
FIG. 4—Continued.

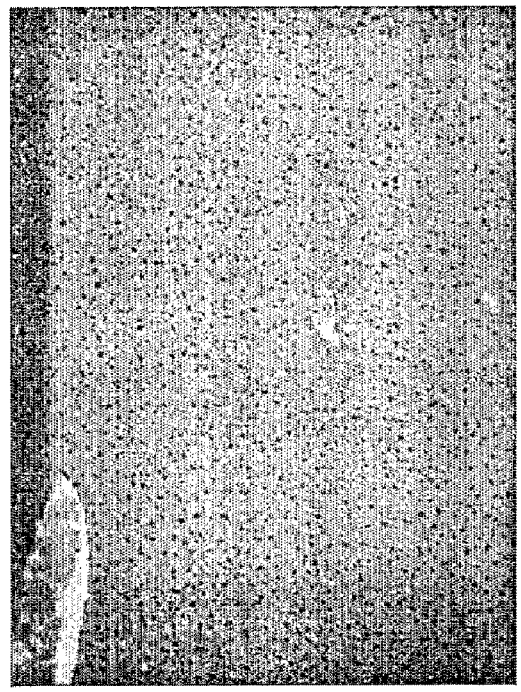
Fig. 12A
Fig. 12B
Magnified acid fast bacterium

SEQUENCE LISTING

```
<160> NUMBER OF SEQ ID NOS: 24

<210> SEQ ID NO 1
<211> LENGTH: 828
<212> TYPE: DNA
<213> ORGANISM: Mycobacterium avium subspecies paratuberculosis
<220> FEATURE:
<223> OTHER INFORMATION: MPT 35 kDa protein DNA encoding sequence

<400> SEQUENCE: 1
atggccaatc cgttcgtcaa ggcgtggaag tacctgatgg cgaagttcaa cgccacgatc      60
gacgagcgcg ccgaccccaa ggtgcagatc aacaggcca tcgaggaagc ccagcgcacc      120
caccaggcgc tgacccagca ggccgctcag gtcatcggca accagcgcca actcgagatg      180
cggctcaacc gccagctcgc cgacgtggag aagctgcagg tcaacgtgcg tcaggcgctg      240
acgctggccg accaggccac cgccgccggc gacaccgcca aggccaccga gtacaacaac      300
gccgccgagg cgttcgccgc ccagctggtc accgccgagc aaagcgtcga agacctcaag      360
acgctgcacg accaggcgct caacgccgcc gcgcaggcca agaaggcggt cgagcagaac      420
gcgatggtgc tgcagcagaa gatcgccgag cgcaccaagc tgctcagcca gctcgaacag      480
gccaagatgc aggaacaggt cagcgcctca ctgcagtcga tgagcgagct ggccgcccc      540 ggcaacgtgc ccagcctgga cgaggtgcgc gacaagatcg agcggcgcta cgccaacgcg      600
atcggggccg ccgaactggc acagggctcc gtgcagggca ggatgctcga ggtcgagcag      660 gccgcgtgc agatggccgg gcattccgg ctcgagcaga tccgcgcctc gatgcgggac      720
gaggcgttgc cgaccggagg cacaccggcc gccggcggca cccaggccgc cccgcgccc      780
```

-continued ggccagggcg ccggcgacgc ggtcagcgag aaaccacttg gtcagtag                828

<210> SEQ ID NO 2
<211> LENGTH: 275
<212> TYPE: PRT
<213> ORGANISM: Mycobacterium avium subspecies paratuberculosis
<220> FEATURE:
<223> OTHER INFORMATION: amino acid sequence of the 35 kDa protein

<400> SEQUENCE: 2

Met Ala Asn Pro Phe Val Lys Ala Trp Lys Tyr Leu Met Ala Lys
                5                  10                  15

Phe Asn Ala Thr Ile Asp Glu Arg Ala Asp Pro Lys Val Gln Ile
                20                  25                  30

Gln Gln Ala Ile Glu Glu Ala Gln Arg Thr His Gln Ala Leu Thr
                35                  40                  45

Gln Gln Ala Ala Gln Val Ile Gly Asn Gln Arg Gln Leu Glu Met
                50                  55                  60

Arg Leu Asn Arg Gln Leu Ala Asp Val Glu Lys Leu Gln Val Asn
                65                  70                  75

Val Arg Gln Ala Leu Thr Leu Ala Asp Gln Ala Thr Ala Ala Gly
                80                  85                  90

Asp Thr Ala Lys Ala Thr Glu Tyr Asn Asn Ala Ala Glu Ala Phe
                95                  100                 105

Ala Ala Gln Leu Val Thr Ala Glu Gln Ser Val Glu Asp Leu Lys
                110                 115                 120

Thr Leu His Asp Gln Ala Leu Asn Ala Ala Gln Ala Lys Lys
                125                 130                 135

Ala Val Glu Gln Asn Ala Met Val Leu Gln Gln Lys Ile Ala Glu
                140                 145                 150

Arg Thr Lys Leu Leu Ser Gln Leu Glu Gln Ala Lys Met Gln Glu
                155                 160                 165

Gln Val Ser Ala Ser Leu Gln Ser Met Ser Glu Leu Ala Ala Pro
                170                 175                 180

Gly Asn Val Pro Ser Leu Asp Glu Val Arg Asp Lys Ile Glu Arg
                185                 190                 195

Arg Tyr Ala Asn Ala Ile Gly Ala Ala Glu Leu Ala Gln Gly Ser
                200                 205                 210

Val Gln Gly Arg Met Leu Glu Val Glu Gln Ala Gly Val Gln Met
                215                 220                 225

Ala Gly His Ser Arg Leu Glu Gln Ile Arg Ala Ser Met Arg Asp
                230                 235                 240

Glu Ala Leu Pro Thr Gly Gly Thr Pro Ala Ala Gly Gly Thr Gln
                245                 250                 255

Ala Ala Pro Ala Pro Gly Gln Gly Ala Gly Asp Ala Val Ser Glu
                260                 265                 270

Lys Pro Leu Gly Gln
                275

<210> SEQ ID NO 3
<211> LENGTH: 1782
<212> TYPE: DNA
<213> ORGANISM: Mycobacterium avium subspecies paratuberculosis
<220> FEATURE:
<223> OTHER INFORMATION: DNA sequence encoding the MptC protein

<400> SEQUENCE: 3

-continued

```
atgagcacga tgattcgtta tttgcttgaa ttacttgacg aacgcggtcg gcgtcacctt      60
cgcgtgatgc ttgccttgca agccgcacag ggaattctgc agggactcgg tttccttttc    120
gtcgtaccgc tgatgggtgt gctcatccac aagccggttg atacgcacgc cctttggtgc    180
tggattgtgg cgatcgccgt cgctgtcgtc gctcaccacg gactgcttgc gtggagcacc    240
tcgctgggtt acctggtcgg cacagatgtg ctgaccagct tcacacccg catcggcaac     300
catctcgcca cgctgccaat cggctggttc cgcaccgatc gcaccggacc gatcgggcgt    360
ctgctcagca aggggaccat ggacgtcgcg gaccttcccg cgcacctgct gcggcatgtc    420
atcgtgggtg tagccgcgcc tgccaccatg atcatcggaa gctatgtgct ggactggcgg    480
gtcgggctcg cattcaccgc cggcgcgctg ctatgcgcac tgacgcttcg actactcatg    540
gtcgtcatcc accgcaacga cgaccagtac gatcacgaca tcggagtgac cgcgtcacgc    600
atcgtcgagt acgcccgtca gcagccgaca ctgcgtgcat acggcgtcct gaaccggccc    660
ggactgggaa cgctagagga atcgcttgtc cggcaacaga cttcgcagtc ccgcttgacc    720
attcgcggcg cgtgggcgct catcggattc ttcggaaccg tccaactggt ggtgaccgcc    780
atcatcgcgc tcaccgtcgc tctcgcagta agcggcagcc ttgcgctttc gacgatggtc    840
ggtttgctga tcatcacctt gcgcatgatc gacccgattt ctcagctcgg cgatctcgcc    900
ggccatgtcc aggtcaacgc cgacgccatc cgccgagtgc gtgaactgtt gacggtaccc    960
ccgttgcccg aacccaccca tccaggtcaa gccacgggtg ccgacatcga attgcagggg   1020
gttcgtttcg cttacgacgg aggtcaaccc accatcgatg gtatcgacgc cgtcttccca   1080
caaggtagcc tgactgccgt cgtcggcccg tctggcgcgg aaaaagcac gctgctcaaa   1140
ctaatcgggc ggttcttcga cgtcgacgaa ggcagcatca ccatcggcgg ctgcgacatc   1200
cgccaactcg gcaccgccgg cgtctcacat ctcacggcgc aagttttcca agacgtgtac   1260
ctctttgaag gcacaattgc cgacaacctg cggatggccg atccgcaagc caccgatgat   1320
gatctccgcc acgtcgccac gatcagtcgc ctcgacgagg tagtcgatcg ccttcccaat   1380
gggtgggaaa cccgcgttgg tgaggcgggg tcgacgctgt ccggcgggga aaagcagcgt   1440
gtctccatag cgcgcgccct gctcaaagac gcaccggtag tactgctgga cgaggcgacc   1500
gcggcgctgg atgccgccaa tgagaccgcc gtttccgacg ctatccacga actagcgcgt   1560
gaccgcacag tcatcgttgt cgcacaccgc cttttcgaccg tggcggccgc cgatcagata   1620
ctggtgctcg acggcggccg gatcaccgag cgtggccgcc acgacacact ggtgggtgcg   1680
ggcggcacct acgcccgctt ctgggaagaa cgaactcgcg cgcgagggtg gcaactcgcg   1740
caaattgcgc ccactcctga actgcaggca cctcgaccat ga                      1782
```

<210> SEQ ID NO 4
<211> LENGTH: 593
<212> TYPE: PRT
<213> ORGANISM: Mycobacterium avium subspecies paratuberculosis
<220> FEATURE:
<223> OTHER INFORMATION: amino acid sequence of the MptC protein

<400> SEQUENCE: 4

Met Ser Thr Met Ile Arg Tyr Leu Leu Glu Leu Leu Asp Glu Arg
                5                  10                  15
Gly Arg Arg His Leu Arg Val Met Leu Ala Leu Gln Ala Ala Gln
            20                  25                  30
Gly Ile Leu Gln Gly Leu Gly Phe Leu Phe Val Val Pro Leu Met
            35                  40                  45

-continued

```
Gly Val Leu Ile His Lys Pro Val Asp Thr His Ala Leu Trp Cys
             50                  55                  60

Trp Ile Val Ala Ile Ala Val Ala Val Ala His His Gly Leu
             65                  70                  75

Leu Ala Trp Ser Thr Ser Leu Gly Tyr Leu Val Gly Thr Asp Val
             80                  85                  90

Leu Thr Ser Phe His Thr Arg Ile Gly Asn His Leu Ala Thr Leu
             95                 100                 105

Pro Ile Gly Trp Phe Arg Thr Asp Arg Thr Gly Pro Ile Gly Arg
            110                 115                 120

Leu Leu Ser Lys Gly Thr Met Asp Val Asp Leu Pro Ala His
            125                 130                 135

Leu Leu Arg His Val Ile Val Gly Val Ala Ala Pro Ala Thr Met
            140                 145                 150

Ile Ile Gly Ser Tyr Val Leu Asp Trp Arg Val Gly Leu Ala Phe
            155                 160                 165

Thr Ala Gly Ala Leu Leu Cys Ala Leu Thr Leu Arg Leu Leu Met
            170                 175                 180

Val Val Ile His Arg Asn Asp Asp Gln Tyr Asp His Asp Ile Gly
            185                 190                 195

Val Thr Ala Ser Arg Ile Val Glu Tyr Ala Arg Gln Gln Pro Thr
            200                 205                 210

Leu Arg Ala Tyr Gly Val Leu Asn Arg Pro Gly Leu Gly Thr Leu
            215                 220                 225

Glu Glu Ser Leu Val Arg Gln Gln Thr Ser Gln Ser Arg Leu Thr
            230                 235                 240

Ile Arg Gly Ala Trp Ala Leu Ile Gly Phe Phe Gly Thr Val Gln
            245                 250                 255

Leu Val Val Thr Ala Ile Ile Ala Leu Thr Val Ala Leu Ala Val
            260                 265                 270

Ser Gly Ser Leu Ala Leu Ser Thr Met Val Gly Leu Leu Ile Ile
            275                 280                 285

Thr Leu Arg Met Ile Asp Pro Ile Ser Gln Leu Gly Asp Leu Ala
            290                 295                 300

Gly His Val Gln Val Asn Ala Asp Ala Ile Arg Arg Val Arg Glu
            305                 310                 315

Leu Leu Thr Val Pro Pro Leu Pro Glu Pro Thr His Pro Gly Gln
            320                 325                 330

Ala Thr Gly Ala Asp Ile Glu Leu Gln Gly Val Arg Phe Ala Tyr
            335                 340                 345

Asp Gly Gly Gln Pro Thr Ile Asp Gly Ile Asp Ala Val Phe Pro
            350                 355                 360

Gln Gly Ser Leu Thr Ala Val Val Gly Pro Ser Gly Ala Gly Lys
            365                 370                 375

Ser Thr Leu Leu Lys Leu Ile Gly Arg Phe Phe Asp Val Asp Glu
            380                 385                 390

Gly Ser Ile Thr Ile Gly Gly Cys Asp Ile Arg Gln Leu Gly Thr
            395                 400                 405

Ala Gly Val Ser His Leu Thr Ala Gln Val Phe Gln Asp Val Tyr
            410                 415                 420

Leu Phe Glu Gly Thr Ile Ala Asp Asn Leu Arg Met Ala Asp Pro
            425                 430                 435

Gln Ala Thr Asp Asp Asp Leu Arg His Val Ala Thr Ile Ser Arg
```

```
                        440                 445                 450
Leu Asp Glu Val Val Asp Arg Leu Pro Asn Gly Trp Glu Thr Arg
                455                 460                 465

Val Gly Glu Ala Gly Ser Thr Leu Ser Gly Gly Glu Lys Gln Arg
                470                 475                 480

Val Ser Ile Ala Arg Ala Leu Leu Lys Asp Ala Pro Val Val Leu
                485                 490                 495

Leu Asp Glu Ala Thr Ala Ala Leu Asp Ala Ala Asn Glu Thr Ala
                500                 505                 510

Val Ser Asp Ala Ile His Glu Leu Ala Arg Asp Arg Thr Val Ile
                515                 520                 525

Val Val Ala His Arg Leu Ser Thr Val Ala Ala Ala Asp Gln Ile
                530                 535                 540

Leu Val Leu Asp Gly Gly Arg Ile Thr Glu Arg Gly Arg His Asp
                545                 550                 555

Thr Leu Val Gly Ala Gly Gly Thr Tyr Ala Arg Phe Trp Glu Glu
                560                 565                 570

Arg Thr Arg Ala Arg Gly Trp Gln Leu Arg Gln Ile Ala Pro Thr
                575                 580                 585

Pro Glu Leu Gln Ala Pro Arg Pro
                590

<210> SEQ ID NO 5
<211> LENGTH: 288
<212> TYPE: DNA
<213> ORGANISM: Mycobacterium avium subspecies paratuberculosis
<220> FEATURE:
<223> OTHER INFORMATION: DNA sequence encoding the ESAT-6 like protein

<400> SEQUENCE: 5
atgtccgacc cgatcactta aacccgggc gcggtggccg acttcgccac cgacgtcgcc      60
tcccgcgccg gccagttgca gtccattttc gacgacacct ccaaccgcac gcacgccctg    120
caggaattct tcgccgggca cggcgcgtcg ggcttttttcg aggcgcaggc ccagatgctg    180
tccgggctgc aggggctcat cgacacgatc cgccagcacg gcagaccac ctcgcacgtg     240 ctggacagcg cgatcagcac ggaccagcac atcgccggcc tgttctga                 288

<210> SEQ ID NO 6
<211> LENGTH: 95
<212> TYPE: PRT
<213> ORGANISM: Mycobacterium avium subspecies paratuberculosis
<220> FEATURE:
<223> OTHER INFORMATION: amino acid sequence of the ESAT-6 like protein

<400> SEQUENCE: 6

Met Ser Asp Pro Ile Thr Tyr Asn Pro Gly Ala Val Ala Asp Phe
                  5                  10                  15

Ala Thr Asp Val Ala Ser Arg Ala Gly Gln Leu Gln Ser Ile Phe
                 20                  25                  30

Asp Asp Thr Ser Asn Arg Thr His Ala Leu Gln Glu Phe Phe Ala
                 35                  40                  45

Gly His Gly Ala Ser Gly Phe Phe Glu Ala Gln Ala Gln Met Leu
                 50                  55                  60

Ser Gly Leu Gln Gly Leu Ile Asp Thr Ile Arg Gln His Gly Gln
                 65                  70                  75

Thr Thr Ser His Val Leu Asp Ser Ala Ile Ser Thr Asp Gln His
                 80                  85                  90
```

Ile Ala Gly Leu Phe
            95

<210> SEQ ID NO 7
<211> LENGTH: 627
<212> TYPE: DNA
<213> ORGANISM: Mycobacterium avium subspecies paratuberculosis
<220> FEATURE:
<223> OTHER INFORMATION: DNA sequence encoding the MptD protein

<400> SEQUENCE: 7

```
atgacggcca ctagctcgac gacccagtcc agtcgccgca tcgacgtccg gatgagcgcc      60
agggatctca tcaacatcgg ggtcttcggc gctctctaca tcgccactgt gttcgcgatc     120
aacgtgttcg ctttcatcaa tccgctcgtc atgttggtcg ccctggcggt cagcatgatc     180
gccggcggcg tgccgttcat gttgttcctc acccgggtgc gacatgcggg catggtgacg     240
gtgtttgcga ttatcacggc cggactgctc gcactgaccg gcacccccc gatctgcttc     300
gtgatcacag ttgcgtgcgc gttggtggcc gaagtcgtcc tgtggctggg acgctatcgc     360
tcccgcacca tgggtgtact ggcgtacgca atctacgcgg cgtggtacat cgggccgctg     420
ctgcccatct tctacgctcg cgatgaatat ttctccagtc ccggcatggc acagatgggt     480
ccgcgctacc tcgaagagat ggaacggttg ttgtcgccag ccgtgctaat cgcattcgac     540
ctgtccacgg tggtattcgg gctgatcggc ggactgctcg gagtaaggtt gctgcgcaag     600
cattttcaga gggccggcct agcttga                                        627
```

<210> SEQ ID NO 8
<211> LENGTH: 208
<212> TYPE: PRT
<213> ORGANISM: Mycobacterium avium subspecies paratuberculosis
<220> FEATURE:
<223> OTHER INFORMATION: MptD amino acid sequence

<400> SEQUENCE: 8

Met Thr Ala Thr Ser Ser Thr Thr Gln Ser Ser Arg Arg Ile Asp
                5                   10                  15

Val Arg Met Ser Ala Arg Asp Leu Ile Asn Ile Gly Val Phe Gly
                20                  25                  30

Ala Leu Tyr Ile Ala Thr Val Phe Ala Ile Asn Val Phe Ala Phe
                35                  40                  45

Ile Asn Pro Leu Val Met Leu Val Ala Leu Ala Val Ser Met Ile
                50                  55                  60

Ala Gly Gly Val Pro Phe Met Leu Phe Leu Thr Arg Val Arg His
                65                  70                  75

Ala Gly Met Val Thr Val Phe Ala Ile Ile Thr Ala Gly Leu Leu
                80                  85                  90

Ala Leu Thr Gly His Pro Pro Ile Cys Phe Val Ile Thr Val Ala
                95                  100                 105

Cys Ala Leu Val Ala Glu Val Val Leu Trp Leu Gly Arg Tyr Arg
                110                 115                 120

Ser Arg Thr Met Gly Val Leu Ala Tyr Ala Ile Tyr Ala Ala Trp
                125                 130                 135

Tyr Ile Gly Pro Leu Leu Pro Ile Phe Tyr Ala Arg Asp Glu Tyr
                140                 145                 150

Phe Ser Ser Pro Gly Met Ala Gln Met Gly Pro Arg Tyr Leu Glu
                155                 160                 165

```
Glu Met Glu Arg Leu Leu Ser Pro Ala Val Leu Ile Ala Phe Asp
            170                 175                 180

Leu Ser Thr Val Val Phe Gly Leu Ile Gly Gly Leu Leu Gly Val
            185                 190                 195

Arg Leu Leu Arg Lys His Phe Gln Arg Ala Gly Leu Ala
            200                 205
```

```
<210> SEQ ID NO 9
<211> LENGTH: 27
<212> TYPE: DNA
<213> ORGANISM: Mycobacterium avium subspecies paratuberculosis
<220> FEATURE:
<223> OTHER INFORMATION: 85A forward primer

<400> SEQUENCE: 9
cgggatccat gatgacgctt gtcgaca                                          27

<210> SEQ ID NO 10
<211> LENGTH: 21
<212> TYPE: DNA
<213> ORGANISM: Mycobacterium avium subspecies paratuberculosis
<220> FEATURE:
<223> OTHER INFORMATION: 85A reverse primer

<400> SEQUENCE: 10
cgggatcctt aggtgccctg g                                                21

<210> SEQ ID NO 11
<211> LENGTH: 20
<212> TYPE: DNA
<213> ORGANISM: Mycobacterium avium subspecies paratuberculosis
<220> FEATURE:
<223> OTHER INFORMATION: 85B forward primer

<400> SEQUENCE: 11
cgggatccat gacagatctg                                                  20

<210> SEQ ID NO 12
<211> LENGTH: 20
<212> TYPE: DNA
<213> ORGANISM: Mycobacterium avium subspecies paratuberculosis
<220> FEATURE:
<223> OTHER INFORMATION: 85B reverse primer

<400> SEQUENCE: 12
cgggatcctt atccgccgcc                                                  20

<210> SEQ ID NO 13
<211> LENGTH: 23
<212> TYPE: DNA
<213> ORGANISM: Mycobacterium avium subspecies paratuberculosis
<220> FEATURE:
<223> OTHER INFORMATION: 85C forward primer

<400> SEQUENCE: 13
cgggatccat gtcgttcatc gaa                                              23

<210> SEQ ID NO 14
<211> LENGTH: 21
<212> TYPE: DNA
<213> ORGANISM: Mycobacterium avium subspecies paratuberculosis
<220> FEATURE:
<223> OTHER INFORMATION: 85C reverse primer

<400> SEQUENCE: 14
```
cgggatcctc aggtggcggg c                                          21

<210> SEQ ID NO 15
<211> LENGTH: 20
<212> TYPE: DNA
<213> ORGANISM: Mycobacterium avium subspecies paratuberculosis
<220> FEATURE:
<223> OTHER INFORMATION: SOD forward primer

<400> SEQUENCE: 15
ggatcctggg actatgcagc                                            20

<210> SEQ ID NO 16
<211> LENGTH: 23
<212> TYPE: DNA
<213> ORGANISM: Mycobacterium avium subspecies paratuberculosis
<220> FEATURE:
<223> OTHER INFORMATION: SOD reverse primer

<400> SEQUENCE: 16
agatcttcag ccgaagatca ggc                                        23

<210> SEQ ID NO 17
<211> LENGTH: 20
<212> TYPE: DNA
<213> ORGANISM: Mycobacterium avium subspecies paratuberculosis
<220> FEATURE:
<223> OTHER INFORMATION: 35 kDa forward primer

<400> SEQUENCE: 17
ggatccccac ttggtgatct                                            20

<210> SEQ ID NO 18
<211> LENGTH: 26
<212> TYPE: DNA
<213> ORGANISM: Mycobacterium avium subspecies paratuberculosis
<220> FEATURE:
<223> OTHER INFORMATION: SOD reverse primer

<400> SEQUENCE: 18
agatcttcac ttgtactcat ggaact                                     26

<210> SEQ ID NO 19
<211> LENGTH: 18
<212> TYPE: DNA
<213> ORGANISM: Mycobacterium avium subspecies paratuberculosis
<220> FEATURE:
<223> OTHER INFORMATION: MptC forward primer

<400> SEQUENCE: 19
ggatcccgcg gtcggcgt                                              18

<210> SEQ ID NO 20
<211> LENGTH: 23
<212> TYPE: DNA
<213> ORGANISM: Mycobacterium avium subspecies paratuberculosis
<220> FEATURE:
<223> OTHER INFORMATION: MptC reverse primer

<400> SEQUENCE: 20
agatcttcat ggtcgaggtg cct                                        23

<210> SEQ ID NO 21
<211> LENGTH: 18
<212> TYPE: DNA
<213> ORGANISM: Mycobacterium avium subspecies paratuberculosis -continued

```
<220> FEATURE:
<223> OTHER INFORMATION: MptD forward primer

<400> SEQUENCE: 21
ggatcccgcc gcatcgac                                                 18

<210> SEQ ID NO 22
<211> LENGTH: 21
<212> TYPE: DNA
<213> ORGANISM: Mycobacterium avium subspecies paratuberculosis
<220> FEATURE:
<223> OTHER INFORMATION: MptD revers primer

<400> SEQUENCE: 22
agatcttcaa gctaggccgg c                                             21

<210> SEQ ID NO 23
<211> LENGTH: 18
<212> TYPE: DNA
<213> ORGANISM: Mycobacterium avium subspecies paratuberculosis
<220> FEATURE:
<223> OTHER INFORMATION: ESAT6-like forward primer

<400> SEQUENCE: 23 ggatcccgg gcgcggtg                                                  18

<210> SEQ ID NO 24
<211> LENGTH: 19
<212> TYPE: DNA
<213> ORGANISM: Mycobacterium avium subspecies paratuberculosis
<220> FEATURE:
<223> OTHER INFORMATION: ESAT6-like reverse primer

<400> SEQUENCE: 24
agatcttcag aacaggccg                                                19
```

COMPOSITIONS FOR ELICITING AN IMMUNE RESPONSE AGAINST *MYCOBACTERIUM AVIUM* SUBSPECIES *PARATUBERCULOSIS*

This application claims priority to U.S. provisional patent application Ser. No. 60/653,536, filed Feb. 16, 2005, the disclosure of which is incorporated herein in its entirety by reference.

FIELD OF THE INVENTION

The present invention relates generally to stimulation of immunological responses, and more specifically to compositions and methods for stimulating prophylactic or and therapeutic immunological responses against *Mycobacterium avium* subspecies *paratuberculosis*.

BACKGROUND OF THE INVENTION

*Mycobacterium avium* subspecies *paratuberculosis* (MPT) is the causative agent of Johne's disease (JD), which causes chronic granulomatous enteritis in ruminants. Clinically affected animals develop chronic diarrhea and progressive weight loss that eventually results in death, while subclinically infected animals mainly have decreased production of milk. JD is of tremendous economic importance to the worldwide dairy industry, causing major losses due to reduced production and early culling of animals with estimates of 20% of U.S. dairy herds affected and costs of $220 million per year to the dairy industry (Wells, et al. 2000. J. Am. Vet. Med. Assoc. 216:1450-1457). Cattle are most susceptible to infection with this organism within the first 6 months of life, but disease typically does not become evident until 3 to 5 years of age. Infection occurs by ingestion of contaminated manure, colostrum, or milk from infected cows (Sweeney, 1996. Vet. Clin. N. Am. Food Anim. Pract. 12:305-312). Fetal infection also occurs, particularly in pregnant cows with advanced disease (Sweeney, et al. 1992. Am. J. Vet. Res. 53:477-80). Although JD is an important infectious disease of ruminants, there is no effective vaccine against this disease. The only currently available vaccine in the United States consists of killed *M. avium* subsp. *paratuberculosis* in an oil adjuvant (Kormendy, B. 1992. Acta Vet. Hung. 40:171-184; Larsen, et l., 1978. Am. J. Vet. Res. 39:65-69). However, such vaccination programs have raised serious public health concerns. For example, at least one veterinarian was accidentally inoculated in the hand during vaccination of animals (Patterson, et al., (1988) J. Am. Vet. Med. Assoc. 192:1197-1199). Further, studies have demonstrated that there is a strong reaction at the injection sites after vaccination with this killed bacteria (Kormendy, B. 1992. Acta Vet. Hung. 40:171-184; Larsen, et l., 1978. Am. J. Vet. Res. 39:65-69). Another drawback of this vaccine is that the vaccinated animals become tuberculin skin test positive (Kormendy, B. 1992. Acta Vet. Hung. 40:171-184; Larsen, et l., 1978. Am. J. Vet. Res. 39:65-69). Thus, there is a need for the development of more effective vaccines against JD that can be used as safe and effective prophylactic and/or therapeutic compositions for MPT infection.

SUMMARY OF THE INVENTION

The present invention provides compositions and methods for stimulating an immunological response in animals against MPT. The compositions comprise immunogenic components which can be MPT antigens or polynucleotides encoding for MPT antigens, or combinations thereof. In one embodiment, the compositions comprise at least five recombinant immunogenic components. Exemplary MPT antigens include MPT 85A, 85B, 85C, 35 kDa, super oxide dismutase (SOD), MptC, MptD and ESAT-6 like protein.

The method comprises administering the composition to an animal in an amount effective to stimulate an immunological response against MPT bacteria. The method is of benefit to any animal susceptible to MPT infection, but is particularly beneficial for ruminants.

Compositions comprising recombinant MPT protein antigens, DNA polynucleotides encoding MPT antigens, or combinations thereof can be formulated with standard pharmaceutical carriers and can be administered via any of a variety of conventional routes. The compositions can be administered at any time to an animal susceptible to contracting MPT infection or an animal that is infected with MPT. However, it is preferable to administer the compositions of the invention prior to MPT infection, such as by administration to pregnant animals who can transfer prophylactic immunologic components to their newborns via colostrum, or by administration during the period from one to five weeks after birth.

BRIEF DESCRIPTION OF THE DRAWINGS

FIGS. 4A-4D are graphical representations of data from analysis of changes in T cell subset distribution in bovine peripheral blood lymphocytes after stimulation with recombinant antigens, as determined by FACS analysis. FIG. 4A. CD4; Ag 85A and Ag 85B induced a higher proportion of $CD4^+$ T lymphocytes in medium shedders compared to low shedders while the percentage of $CD4^+$ lymphocytes was unchanged in non-infected control cattle. FIG. 4B. CD8; Ag 85A increased the proportion of $CD8^+$ T lymphocytes in medium shedders, while the increased percentage of $CD8^+$ lymphocytes was very low in non-infected cattle. FIG. 4C. CD25; Ag 85A and Ag85B increased the proportion of $CD25^+$ T cells in both shedder groups while they had little effect in non-infected cattle. In contrast, Ag 85C and the 35-kDa protein significantly increased the proportion of $CD25^+$ T cells only in the medium shedders ($P<0.05$). FIG.

4D. $\gamma\delta^+$ T-cells; all antigens resulted in significantly lower increases in all cell subsets in both the low and medium shedder groups except SOD for $\gamma\delta^+$ T cells in medium shedders.

Figure 5:
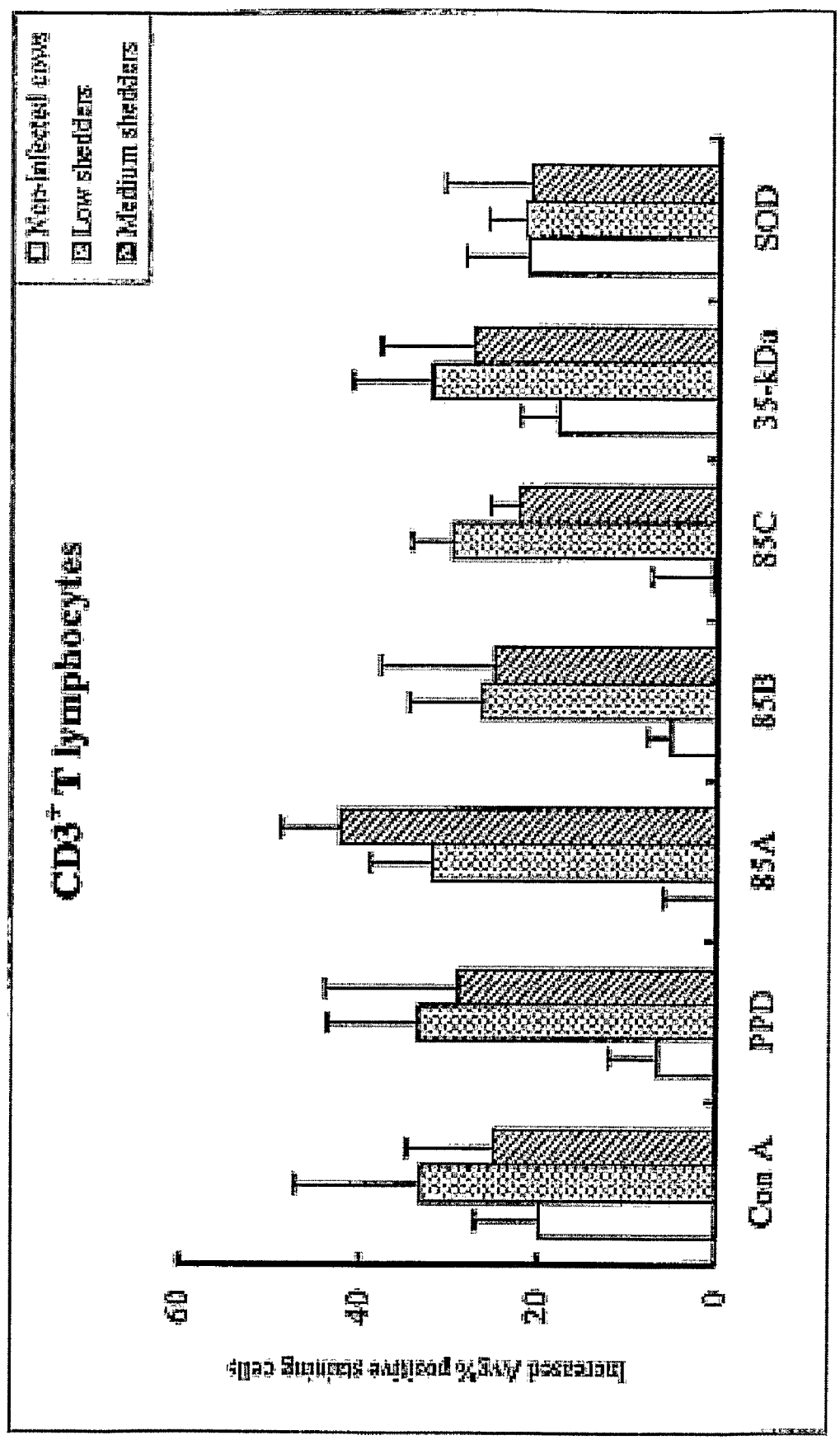

FIG. 5 is a graphical representation of data from analysis of differential changes of $CD3^+$ T lymphocytes in response to stimulation with recombinant proteins and two controls (ConA and PPD). Data are expressed as the average of cells staining positive for CD3 (1 standard error of the mean) in response to each recombinant antigen relative to the shedding level.

Figure 6:
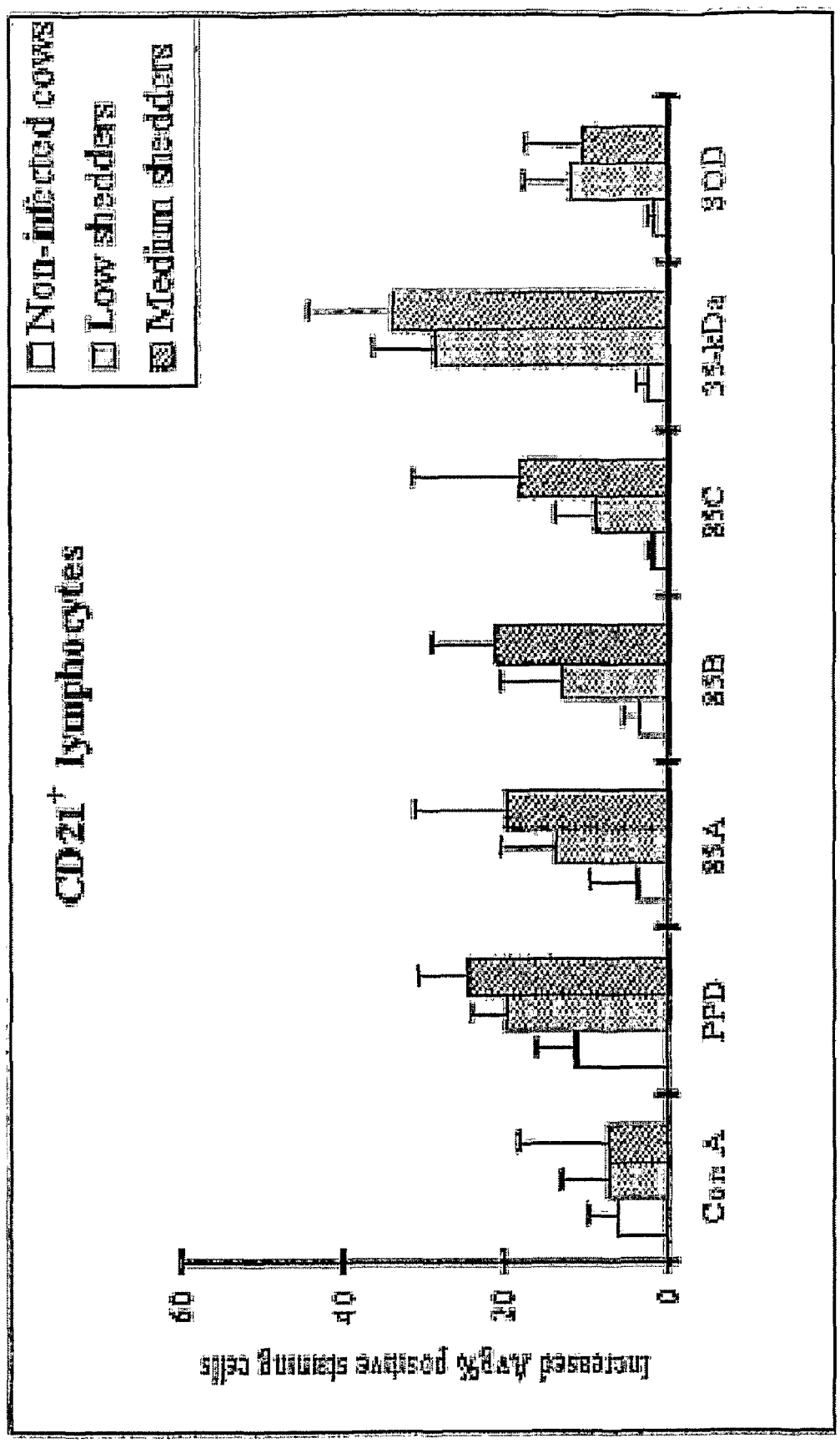

FIG. 6 is a graphical representation of data from analysis of increased $CD21^+$ B lymphocyte subsets in bovine peripheral blood lymphocytes after stimulation with recombinant antigens, as determined by FACS analysis. The results are reported as the average percent increase in positive-staining cells and the error bars represent 1 standard error of the mean (SEM). Recombinant 35-kDa protein induced the largest increase in $CD21^+$ B lymphocytes in medium shedders. No significant increase in the proportion of B lymphocytes was observed in response to the other antigens regardless of bacterial shedding levels ($P>0.05$).

Figure 7:
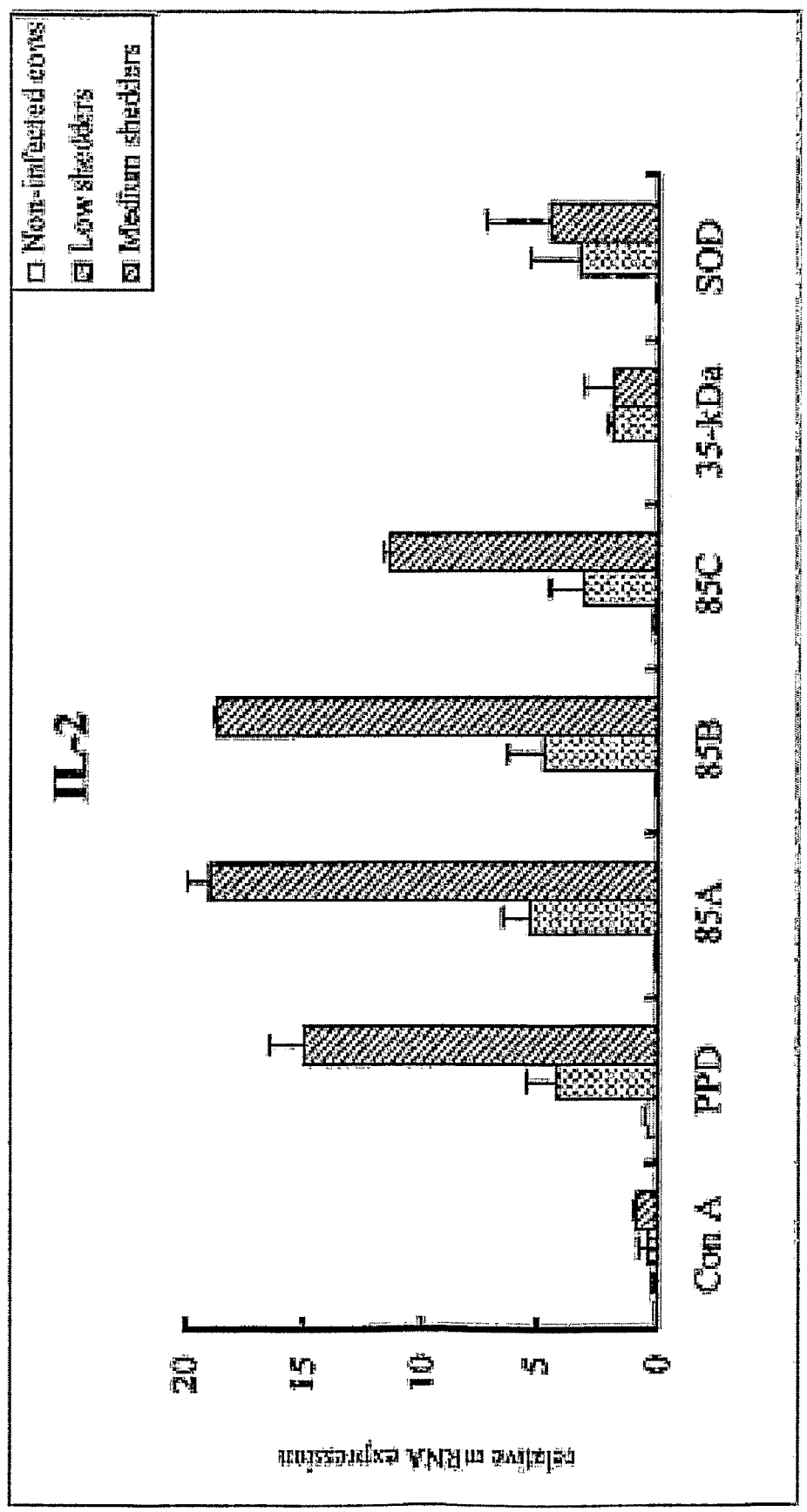

FIG. 7. is a graphical representation of data from analysis of IL-2 profiles of bovine PBMCs from non-infected cattle, low and medium shedders after stimulation with recombinant antigens for 24 hrs. Results represent the mean fold increases of IL-4 over un-stimulated PBMCs, which served as calibrators. Ags 85 A and B most strongly stimulated medium shedders while the 35 kDa protein and SOD had lesser effects ($p<0.05$).

Figure 8A:
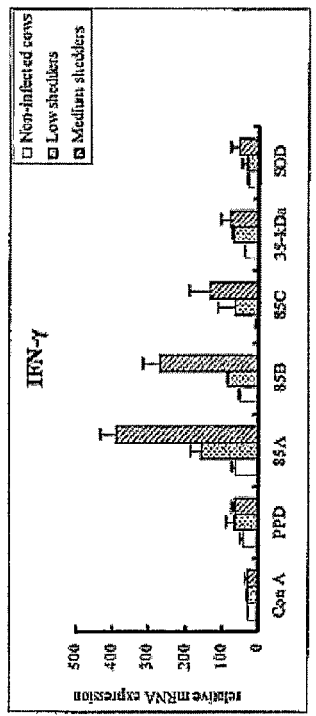
Figure 8B:
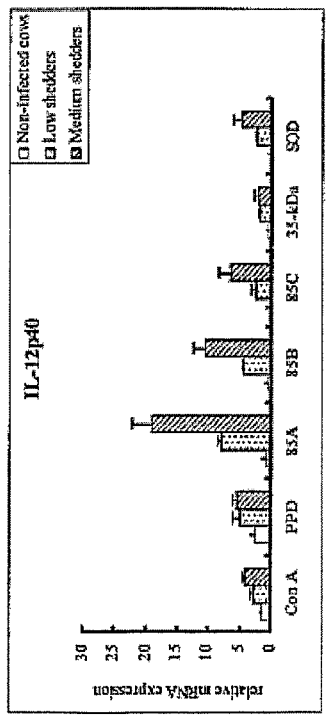
Figure 8C:
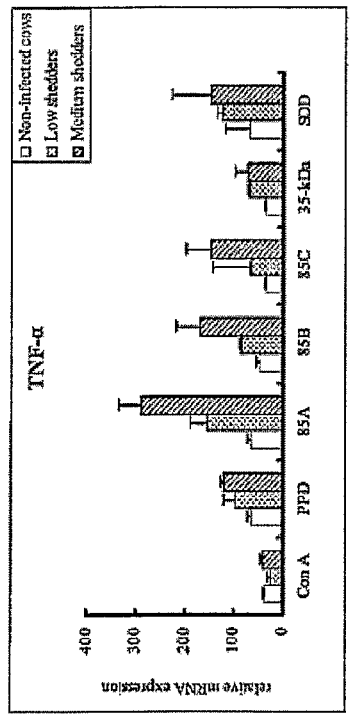

FIGS. 8A-8C are graphical representations of data from analysis of comparison of cytokine mRNA profiles for IFN-γ (FIG. 8A), IL-12p40 (FIG. 8B) and TNF-α (FIG. 8C) of bovine PBMCs from non-infected cattle, low and medium shedders after stimulation with recombinant antigens for 24 hrs. Results represent the mean fold increase over un-stimulated PBMCs, which served as calibrators. The results are similar with Ags 85 A and B most strongly stimulating medium shedders while the 35 kDa protein and SOD had lesser effects.

Figure 9:
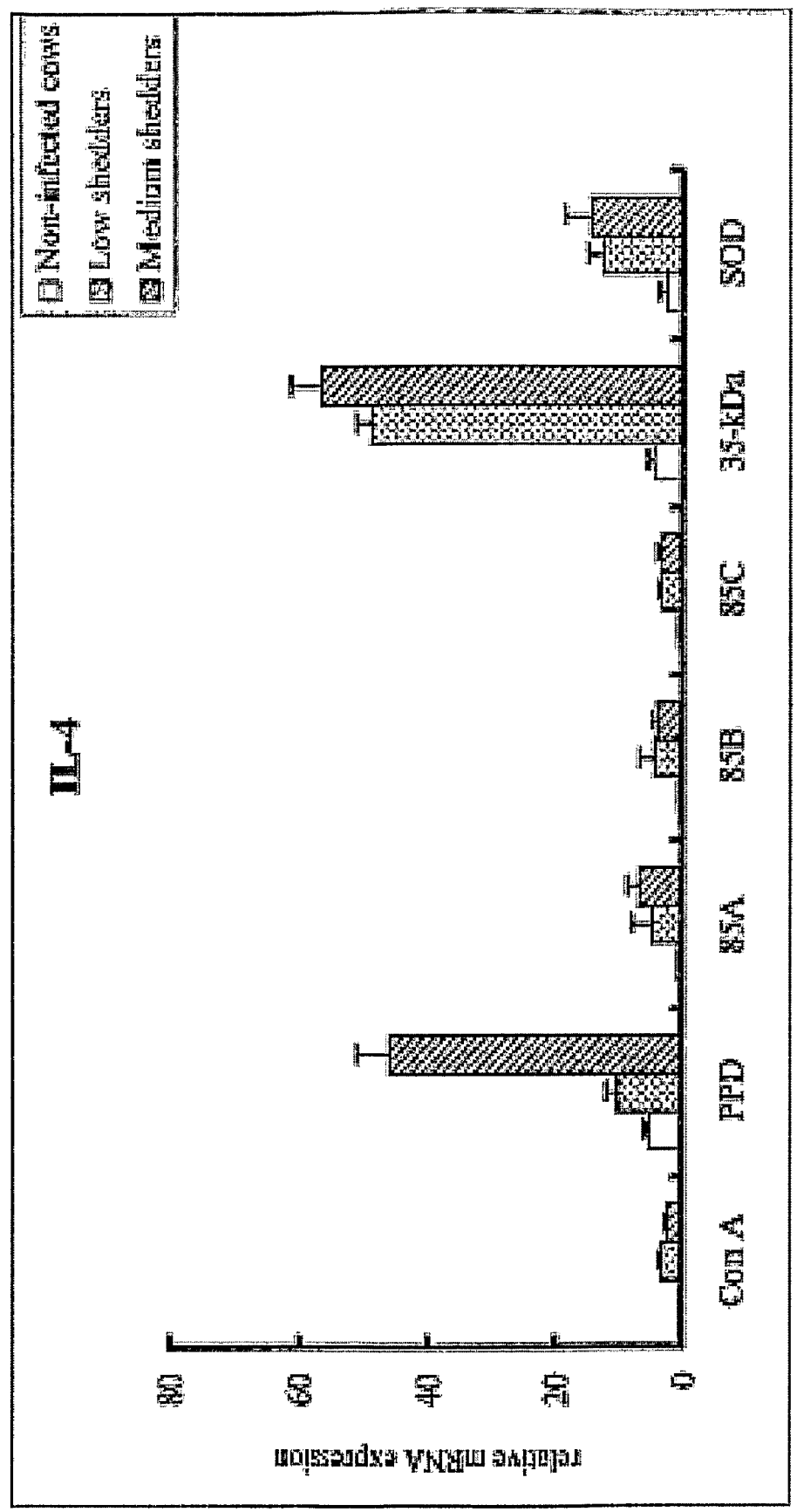

FIG. 9. is a graphical representation of data from analysis of IL-4 mRNA profiles of bovine PBMCs from non-infected cattle, low and medium shedders after stimulation with recombinant antigens for 24 hrs. Results represent the mean fold increases of IL-4 over un-stimulated PBMCs, which served as calibrators. The 35-kDa protein strongly stimulated IL-4 mRNA expression in both low and medium shedders.

Figure 10A:
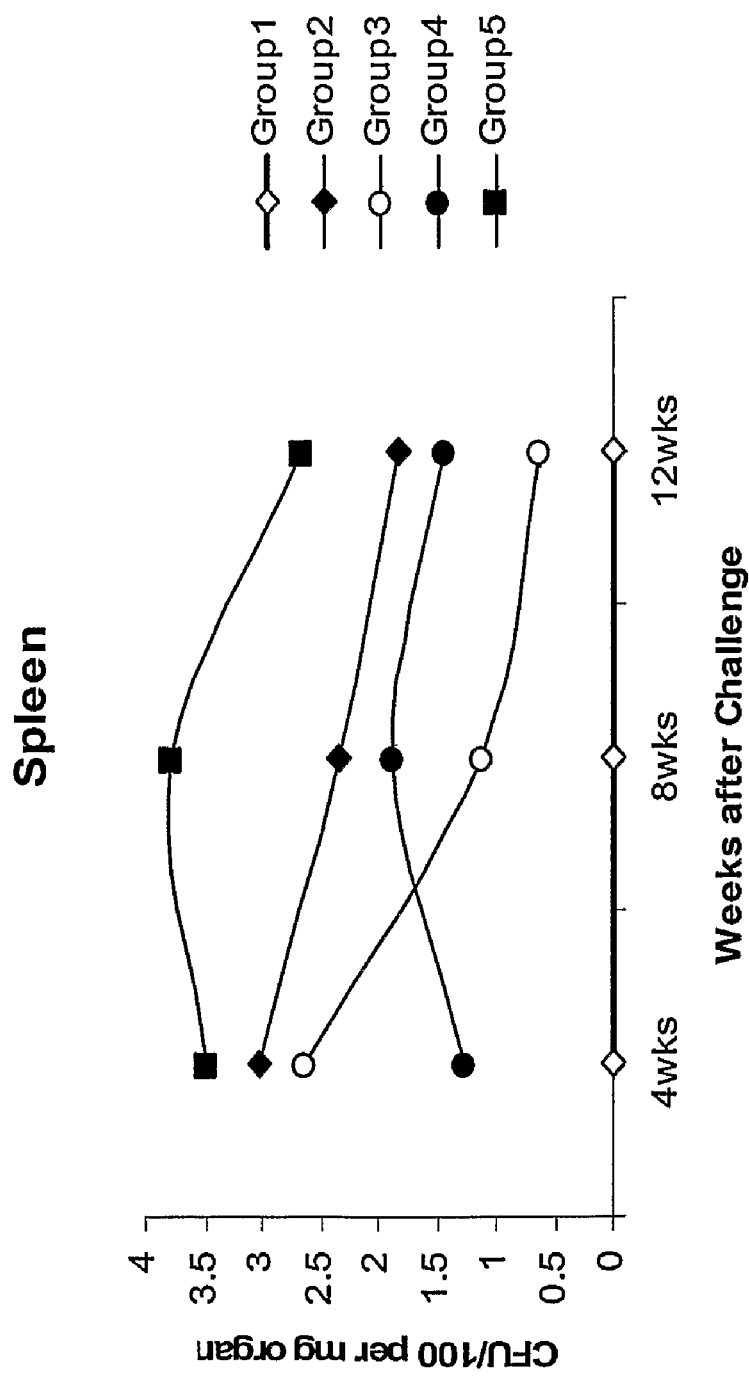
Figure 10B:
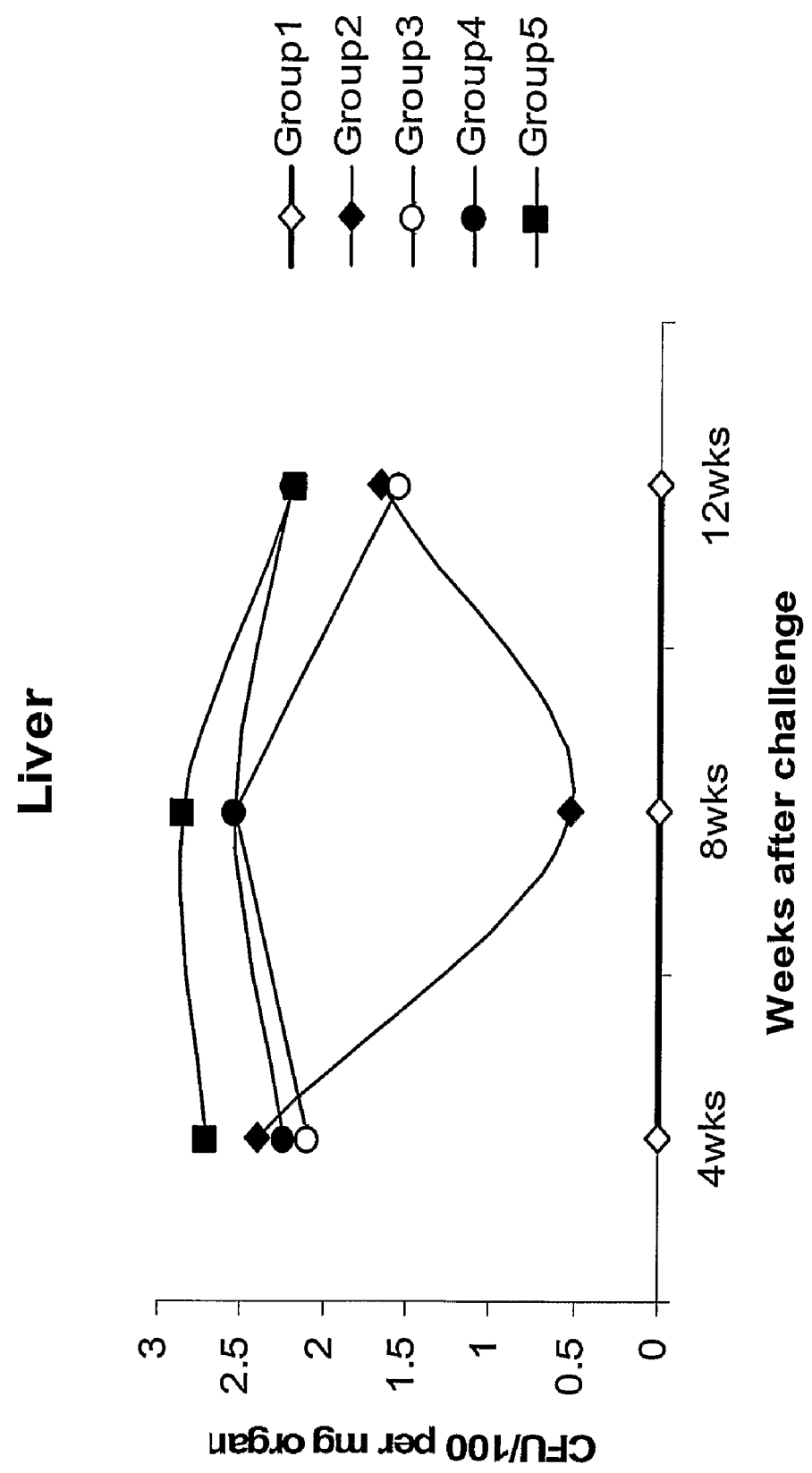

FIG. 10 is a graphical representation of bacterial recovery from spleen and liver after administration of the indicated DNA constructs and controls and subsequent challenge with MPT.

Figure 11A:
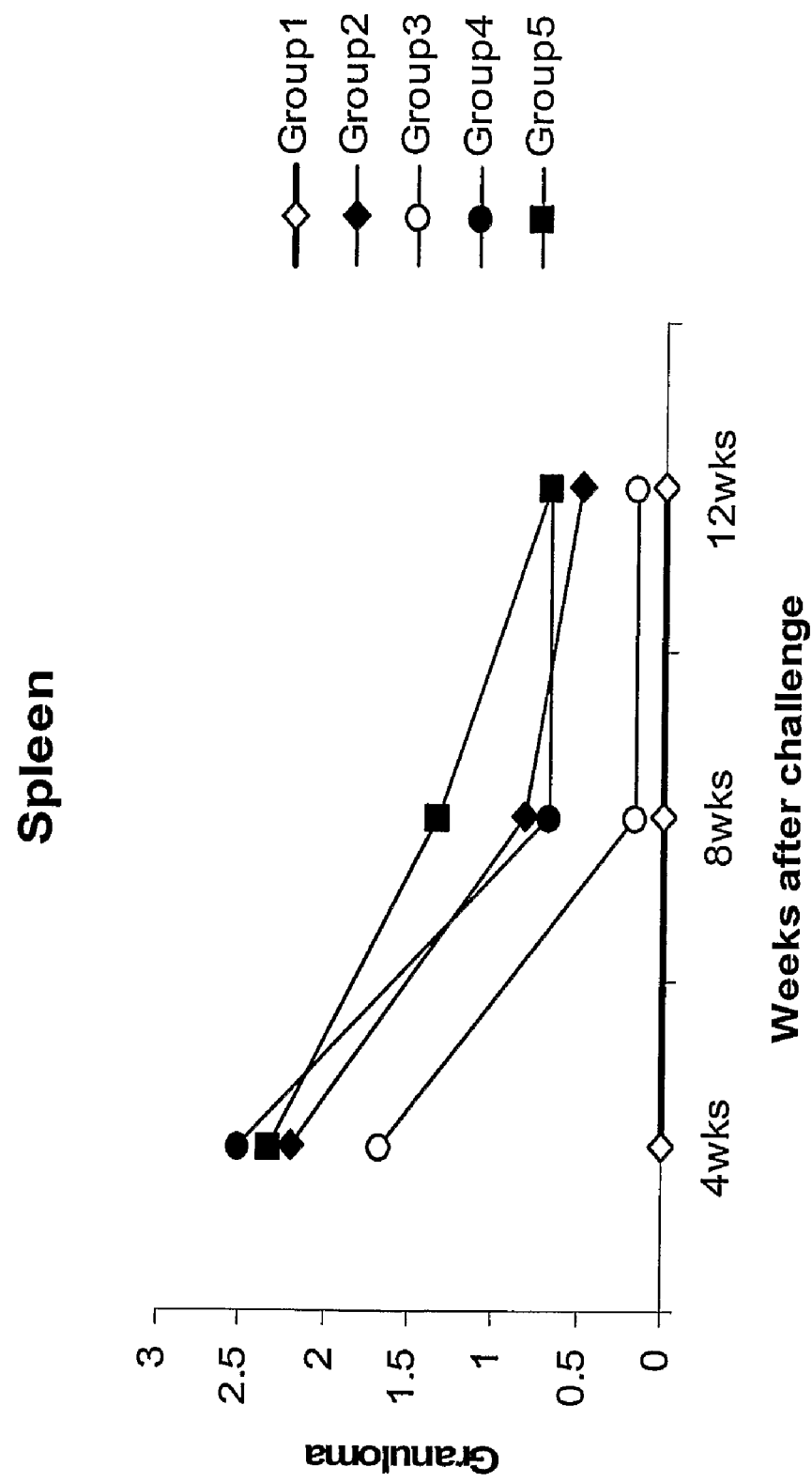
Figure 11B:
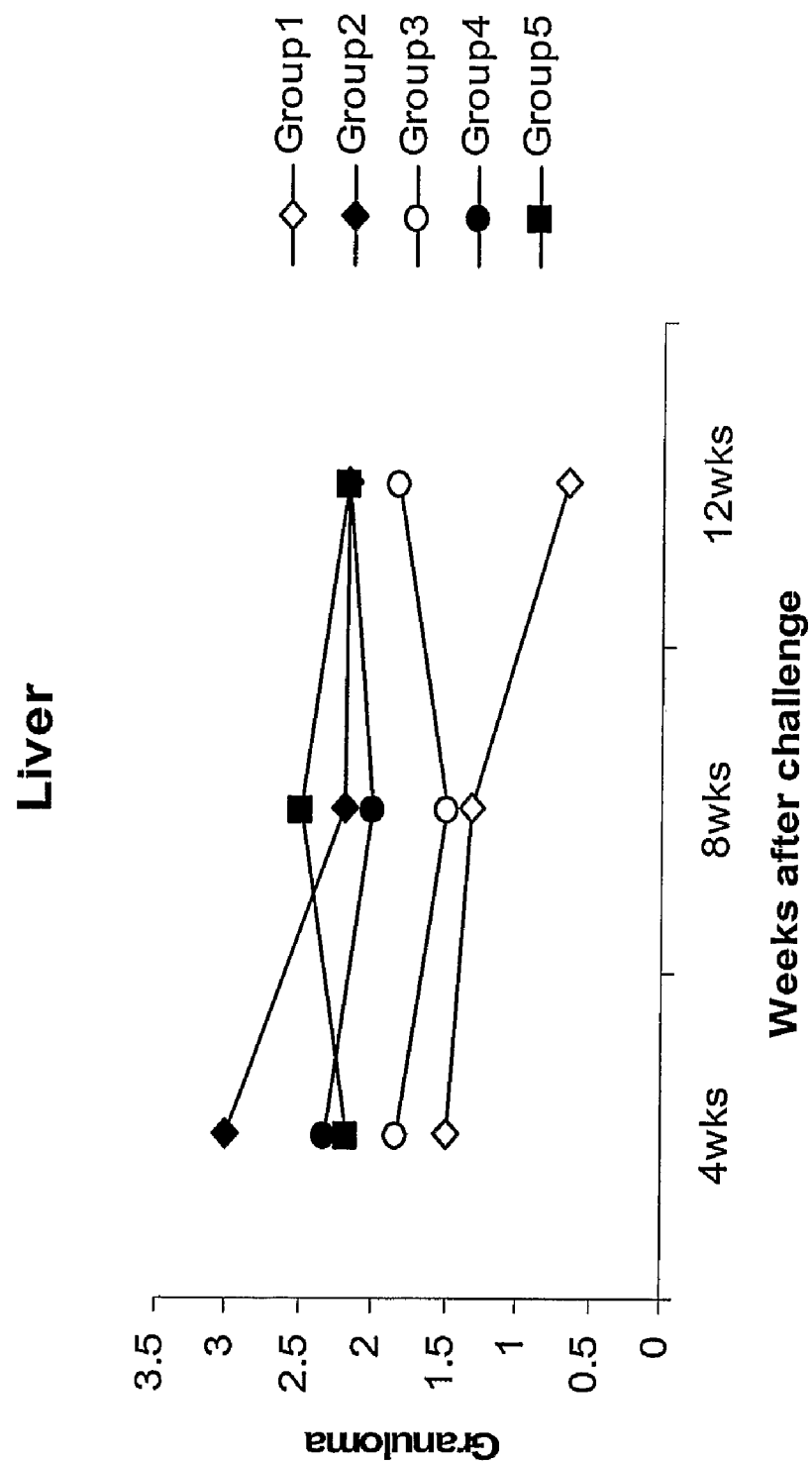

FIG. 11 is a graphical representation of the mean number of granulomas in spleen and liver after administration of the indicated DNA constructs and controls and subsequent challenge with MPT.

FIGS. 12A and 12B are photographic representations of Ziehl-Neelsen staining of tissues revealing numerous acid-fast bacilli (FIG. 12A). In contrast, the infection was much less severe in the mice vaccinated with the MPT DNA constructs encoding all five antigens (FIG. 12B).

DETAILED DESCRIPTION OF THE INVENTION

The present invention provides compositions and methods for stimulating an immunological response against MPT in an animal. The compositions comprise DNA polynucleotides encoding MPT antigens, MPT antigens, or combinations thereof. In one embodiment, at least five immunogenic components are selected from recombinant MPT antigens and DNA polynucleotides. The method comprises administering the composition to an animal in an amount effective to stimulate an immunological response against MPT bacteria.

As used herein, an "immunological component" is a component of the composition that can directly or indirectly stimulate an immunological response. Accordingly, when introduced into an animal, expression vectors comprising DNA polynucleotides encoding MPT antigens enter cells of the animal and express MPT antigens. The expressed MPT antigens in turn stimulate an immunological response. Thus, a DNA polynucleotide encoding an MPT antigen is considered an immunogenic component which indirectly stimulates an immunological response. In respect of an administered MPT protein antigen, since the antigen is recognized directly by the immune system, the antigen is considered an immunogenic component which directly stimulates an immunological response.

The method can provide benefit to any animal susceptible to MPT infection, where infection is considered to mean colonization of the intestinal mucosa of the animal by MPT. However, the compositions and method are particularly well suited for prophylaxis or therapy for MPT infection of ruminants, including but not limited to cattle, sheep, goats, deer and elk, antelope, and buffalo.

Thus, the compositions can be administered to any MPT infected or non-infected animal. Administration of the compositions to infected animals according to the method of the invention is considered to stimulate a therapeutic immunological response. However, it is preferable to administer the compositions prior to MPT infection to stimulate a prophylactic response. For example, the compositions can be administration to a pregnant animal who can transfer prophylactic immunologic components to their non-infected newborns via colostrum. Alternatively, the compositions can be administered during the period from one to five weeks after birth to provide a prophylactic effect which can prevent infection or reduce the severity of disease if infection occurs. Thus, in one embodiment, the method of the invention is prophylactic for MPT infection, while in another embodiment, the method is therapeutic for MPT infection. The method can also be used for prophylaxis or therapy of Johne's Disease.

Suitable MPT antigens for use in the invention include but are not limited to MPT proteins 85A, 85B, 85C, 35 kDa, SOD, MptC, MptD and ESAT-6 like protein. Recombinant MPT protein antigens can be obtained for use in the invention by techniques known to those skilled in the art, such as by conventional recombinant cloning methods. Suitable DNA cloning procedures and methods for expressing and purifying recombinant proteins are known. (See, for example, Sambrook et al. 2001, *Molecular cloning: a laboratory manual,* 3rd ed. Cold Spring Harbor Laboratory Press, New York, N.Y.). In general, to obtain recombinant MPT protein antigens, MPT genomic DNA can be obtained from an MPT culture according to standard methods, such as by the well known alkaline lysis procedure. The DNA encoding the antigens can be amplified, such as by the polymerase chain reaction, from the genomic DNA and the amplification products can be cloned individually or in various combinations into a one or more suitable expression vectors. Appropriate host cells can be transfected with the expression vector and the transfected cells can be cultured under appropriate conditions for expression of the antigens. The antigens can be subsequently extracted and purified from the culture according to standard techniques.

For administration to animals, suitably purified recombinant MPT antigens can be combined with standard pharmaceutical carriers. Acceptable pharmaceutical carriers for use with proteins are described in Remington's Pharmaceutical Sciences (18th Edition, A. R. Gennaro et al. Eds., Mack Publishing Co., Easton, Pa., 1990). Further, the antigens may be provided in conventional liposomal or microsomal formulations.

Compositions comprising the MPT antigens for use in stimulating an immunological response can be administered by any acceptable route. Suitable routes of administration include oral, mucosal and parenteral (e.g., intravascular, intramuscular, and subcutaneous injection). Those skilled in the art will recognize that the amount of antigens administered to a particular animal will depend on a number of factors such as the route of administration, and the size, physical condition and the MPT status of the animal. The relative amounts of each antigen in a formulation can be adjusted according to known parameters, such as to provide molar equivalents or other ratios of the antigens. Further, the compositions can be used in a single administration or in a series of administrations to boost the immunological response to the MPT antigens. In general, a total dosage of between 10-200 μg of protein can be administered. When DNA encoding MPT antigens is administered, in general, between 30-500 μg of DNA can be administered.

In one embodiment, the method of the invention comprises administration of a composition comprising at least five recombinant MPT antigens. For example, MPT antigens 85A, 85B, 85C, 35 kDa antigen and superoxide dismutase (SOD) can be administered in a single formulation. 85A, 85B and 85C are fibronectin-binding proteins; the 35 Kda and SOD proteins are outer surface proteins. The DNA sequence encoding the MTP 85A gene and the amino acid sequence of the 85A gene, is provided in GenBank accession no. AF280067 (Oct. 10, 2003, entry). The DNA sequence encoding the MTP 85B gene and the amino acid sequence of the 85A gene is provided in GenBank accession no. AF219121 85B gene (Nov. 21, 2002 entry). The DNA sequence encoding the MTP 85C gene and the amino acid sequence of the 85C gene is provided in GenBank accession no. AF280068 (Nov. 21, 2002 entry). The DNA sequence encoding the MTP SOD gene and the amino acid sequence of the SOD gene is provided in GenBank accession no. AF180816 (Nov. 30, 2001 entry). The DNA sequence encoding the 35 kDa protein is provided herein as SEQ ID NO:1. The amino acid sequence of the 35 kDa protein is provided herein as SEQ ID NO:2. Additional MPT include MptC, MptD and ESAT-6 like protein. The DNA sequence encoding the MptC protein is provided herein as SEQ ID NO:3. The amino acid sequence of the MptC protein is provided herein as SEQ ID NO:4. The DNA sequence encoding the ESAT-6 like protein is provided herein as SEQ ID NO:5. The amino acid sequence of the ESAT-6 like protein is provided herein as SEQ ID NO:6. The DNA sequence encoding the MptD sequence is provided herein as SEQ ID NO:7. The DNA sequence encoding the MptD amino acid sequence is provided herein as SEQ ID NO:8.

The DNA sequences of primers used to amplify DNA encoding the MPT antigens used herein from genomic MPT DNA are provided in Table 1.

TABLE 1

| Gene/ primer name | SEQ ID: NO | Primer Sequence (5'->3') | Length of DNA product (bp) | Accession No. of ss amplification product and amino acid sequence of antigen |
|---|---|---|---|---|
| 85A | | | | |
| pVR85AF | 9 | CGGGATCCATGATGACGCTTGTCGACA | 1050 | AF280067 |
| pVR85AR | 10 | CGGGATCCTTAGGTGCCGTGG | | |
| 85B | | | | |
| pVR85BF | 11 | CGGGATCCATGACAGATCTG | 1000 | AF219121 |
| pVR85BR | 12 | CGGGATCCTTATCCGCCGCC | | |
| 85C | | | | |
| pVR85CF | 13 | CGGGATCCATGTCGTTCATCGAA | 1100 | AF280068 |
| pVR85CR | 14 | CGGGATCCTCAGGTGGCGGGC | | |
| SOD | | | | |
| pVRSODF | 15 | GGATCCTGGGACTATGCAGC | 590 | AF180816 |
| pVRSODR | 16 | AGATCTTCAGCCGAAGATCAGGC | | |
| 35 Kda (MAP2121c) | | | | |
| pVR35KDF | 17 | GGATGCCGACTTGGTGATGT | 910 | |
| pVR35KDR | 18 | AGATCTTCACTTGTACTCATGGAACT | | |
| MptC (MAP 3734) | | | | |
| pVRMPTCF | 19 | GGATCCGGCGGTCGGCGT | 1750 | |
| pVRMPTCR | 20 | AGATCTTCATGGTCGAGGTGCCT | | |

TABLE 1-continued

| Gene/ primer name | SEQ ID: NO | Primer Sequence (5'->3') | Length of DNA product (bp) | Accession No. of ss amplification product and amino acid sequence of antigen |
|---|---|---|---|---|
| MptD (MAP 3733) | | | | |
| pVRMPTDF | 21 | GGATCCCGCCGCATCGAC | 600 | |
| pVRMPTDR | 22 | AGATCTTCAAGCTAGGCGGGC | | |
| ESAT 6 Like (MAP 0161) | | | | |
| pVRESATF | 23 | GGATCCCCGGGCGCGGTG | 270 | |
| pVRESATR | 24 | AGATCTTCAGAACAGGCCG | | |

In another embodiment, compositions comprising DNA polynucleotides which encode five or more MPT antigens can be prepared. MPT antigen encoding sequences can be obtained by amplification of MPT genomic DNA using appropriate primers and inserting the amplification products into expression vectors in the same manner as described for preparation of recombinant antigen proteins.

Suitable expression vectors contain appropriate eukaryotic transcription and translation signals, and may contain additional elements, such as polyadenylation and/or protein trafficking signals. One example of a suitable expression vector is pVR1020 (available from Vical, Inc., San Diego, Calif.), which contains an immediate-early cytomegalovirus promoter to promote efficient expression in a eukaryotic host, as well as a plasminogen activator secretion signal to facilitate secretion of the antigens from the cells of the eukaryotic host.

It will be recognized by those skilled in the art that one or more distinct expression vectors, as distinguished from one another by the MPT antigens they encode and/or by their regulatory or other elements, such as polycloning sites, will be used in the instant method. Thus, a single expression vector encoding at least five MPT antigens, or at least five expression vectors each encoding a different MPT antigen, or combinations of expression vectors each encoding at least one MPT antigen, can be used in the present method to deliver polynucleotides encoding at least five MPT antigens.

In one embodiment, DNA polynucleotide sequences encoding MPT antigens 85A, 85B, 85C, SOD, MptC, MptD, 35 kDa, and ESAT6-like proteins can be provided in separate expression vectors that can be used for protein expression and purification and for administration in various combinations to animals for stimulating an immune response.

The expression vectors encoding the MPT antigens may be formulated in any pharmaceutically effective preparation for administration to the animals. Such formulations may be, for example, a saline solution such as phosphate buffered saline (PBS). It is preferred to utilize pharmaceutically acceptable formulations which also provide long-term stability of the DNA. Thus, it is preferable to remove and/or chelation trace metal ions from the formulation buffers or from vials and closures in which the DNA is stored to stabilize and protect the DNA during storage. In addition, inclusion of non-reducing free radical scavengers, such as ethanol or glycerol, is useful to prevent damage of the DNA from free radical production that may still occur, even in apparently demetalated solutions. Further, the DNA may be provided in conventional liposomal or microsomal formulations.

There is no limitation to the route that the DNA polynucleotides of the invention can be delivered, so long as their delivery stimulates an immunological response against MPT in the recipient animals. Accordingly, the DNA polynucleotides of the present invention can be administered to the animal by any means known in the art, such as enteral and parenteral routes. These routes of delivery include but are not limited to intramusclar injection, intraperitoneal injection, intravenous injection, and oral delivery. A preferred route is intramuscular.

In another embodiment, the composition of the invention comprises at least five immunogenic components which are provided as a combination of MPT protein antigens and DNA polynucleotides encoding MPT antigens. Such compositions can be obtained by combining the recombinant MPT antigens described herein and the polynucleotides encoding MPT proteins described herein. In this regard, the polynucleotide sequences can be present in one or more expression vectors and the MPT antigens can be provided as recombinant proteins. Compositions comprising recombinant MPT antigens and polynucleotides encoding MPT antigens can be combined with conventional pharmaceutical carriers and administered as described herein and/or according to standard techniques. Conventional liposomal or microsomal preparations of the recombinant MPT antigens and polynucleotides encoding MPT antigens can be provided. Further, and as will be recognized by those skilled in the art, whether or not the compositions comprise recombinant antigens alone as the immunogenic components, DNA polynucleotides alone as the immunogenic components, or combinations of recombinant antigens and DNA polynucleotides encoding the recombinant antigens as the immunogenic components, the compositions of the invention may further comprise a suitable adjuvant.

Thus, and without intending to be bound by any particular theory, administration of the recombinant MPT antigens, polynucleotides encoding recombinant antigens, and/or combinations thereof according to the method of the invention is believed to stimulate an immunological response that can be prophylactic or therapeutic with respect to MPT infection.

The following examples describe the various embodiments of this invention. These examples are illustrative and are not intended to be restrictive.

Example 1

This Example provides a comparison of distinct lymphoproliferation effectis in response to stimulation with individual antigens.

To examine lymphoproliferative responses, five MPT recombinant antigens, 85A, 85B, 85C, 35 kDa antigen and superoxide dismutase (SOD), were analyzed for their ability to elicit proliferative responses in PBMCs obtained from cows with different MPT shedding levels. For this and other Examples as indicated herein, a total of 38 Holstein cows, 2 to 3 years old, were divided into 3 groups. Healthy controls (n=18) were negative for MPT infection as determined by negative fecal culture and negative IS900 PCR testing. The healthy controls came from a farm that has been fecal culture and IS900 PCR negative for the past ten years. Positive animals were subdivided into low shedders (n=16) and medium shedders based on the number of colony forming units (CFU)/gram of feces (n=4). Low shedders are considered animals with 1-30 CFU/gram of feces. Medium shedders are considered animals with between 31-300 CFU/gram of feces. Heavy shedders (>300 CFU/gm feces) were unavailable since they are culled immediately from farms once they are identified. Fecal cultures and IS900 PCR testing to determine MPT infection status were preformed as previously described (Shin et al, (2004) J. Vet. Diagn. Invest. 16:116-120).

For use in lymphprolifations assays, recombinant antigens 85A, 85B, 85C, 35 kDa antigen and SOD were cloned and expressed using standard techniques and as previously described. (Dheenadhayalan et al., (2002) DNA Seq. 13:287-294; Shin et al., (2004) J. Vet. Sci. 5:111-117) and purified as previously described (Skeiky et al., (1998) J. Immunol. 161: 6171-6179). The antigens used in these Examples had negligible (10 pg/ml) endotoxin in a Limulus amebocyte assay.

For isolation and culture of bovine peripheral blood mononuclear cells, peripheral blood (20 ml) of all cows was collected from the tail vein with heparinized vacuum tubes. Isolation of lymphocytes from heparinized blood was performed by differential centrifugation using HISTOPAQUE 1.077 (Sigma). Twenty ml of heparinized whole blood was layered over 15 ml HISTOPAQUE in a 50-ml sterile polypropylene tube (Falcon) and then centrifuged at 1000×g for 30 min at room temperature. The plasma layer was discarded and the mononuclear cell layer was carefully collected and washed three times with phosphate-buffered saline (PBS, pH 7.2). Contaminating red blood cells were lysed with 0.87% ammonium KCl buffer by inverting for 2 min at room temperature, then immediately adding 30 ml PBS.

The washed cell pellets were suspended in PBS and counted using a hemacytometer and trypan blue to determine percent viability. Differential cell counts consistently showed greater than 96% lymphocytes, 1% monocytes and less than 3% granulocytes in the cell suspension.

The lymphocytes were resuspended at $2 \times 10^6$/ml in RPMI 1640 containing 10% endotoxin free FCS (Cellect Gold; ICN Biomedicals, Inc., Costa Mesa, Calif.), 2 mM L-glutamine, 10 mM HEPES, 100 IU/ml Penicillin, 100 µg/mL streptomycin and 50 µg/mL gentamycin (Sigma) and 250 ul were added to either 96-well round-bottomed plates or flat-bottomed plates, depending on the purposes of the experiment.

To investigate lymphocyte proliferation in response to the individual antigens, a blastogenesis assay was performed. Briefly, PBMCs were initially incubated in a 96-well flat-bottomed microplate for 3 days at 37 C in a humidified atmosphere with 5% $CO_2$. Cultures were then stimulated with Con A (10 µg/mL), purified protein derivative (PPD) (each positive controls) (10 µg/mL) or each purified recombinant protein (10 µg/mL) and 40 µl (1.0 µCi) of methyl-3H-thymidine (PerkinElmer Life Science Inc, MA, USA) in culture medium were added to each well. The cells were incubated for an additional 18 h in the same conditions, and the cells were then harvested using a semi automatic cell harvester (Skatronas Liter Norway). Blastogenic activity was recorded as counts per minute (cpm) of radioactivity based on liquid scintillation counting. Results were expressed as stimulation indices (SI) calculated as follows:

$$SI \text{ (stimulation Index)} = \frac{(CPM \text{ of antigen stimulated positive culture}) - (CPM \text{ of background})}{(CPM \text{ of control culture or Negative}) - (CPM \text{ of background})}$$

For this and other Examples herein, statistical analysis of data was performed in Excel and GraPad Prism software package version 2.0. Differences between individual groups, antigens and cytokine gene expression were analyzed with the Student's t-test. Differences were considered significant if probability values of $P<0.05$ were obtained.

Figure 1:
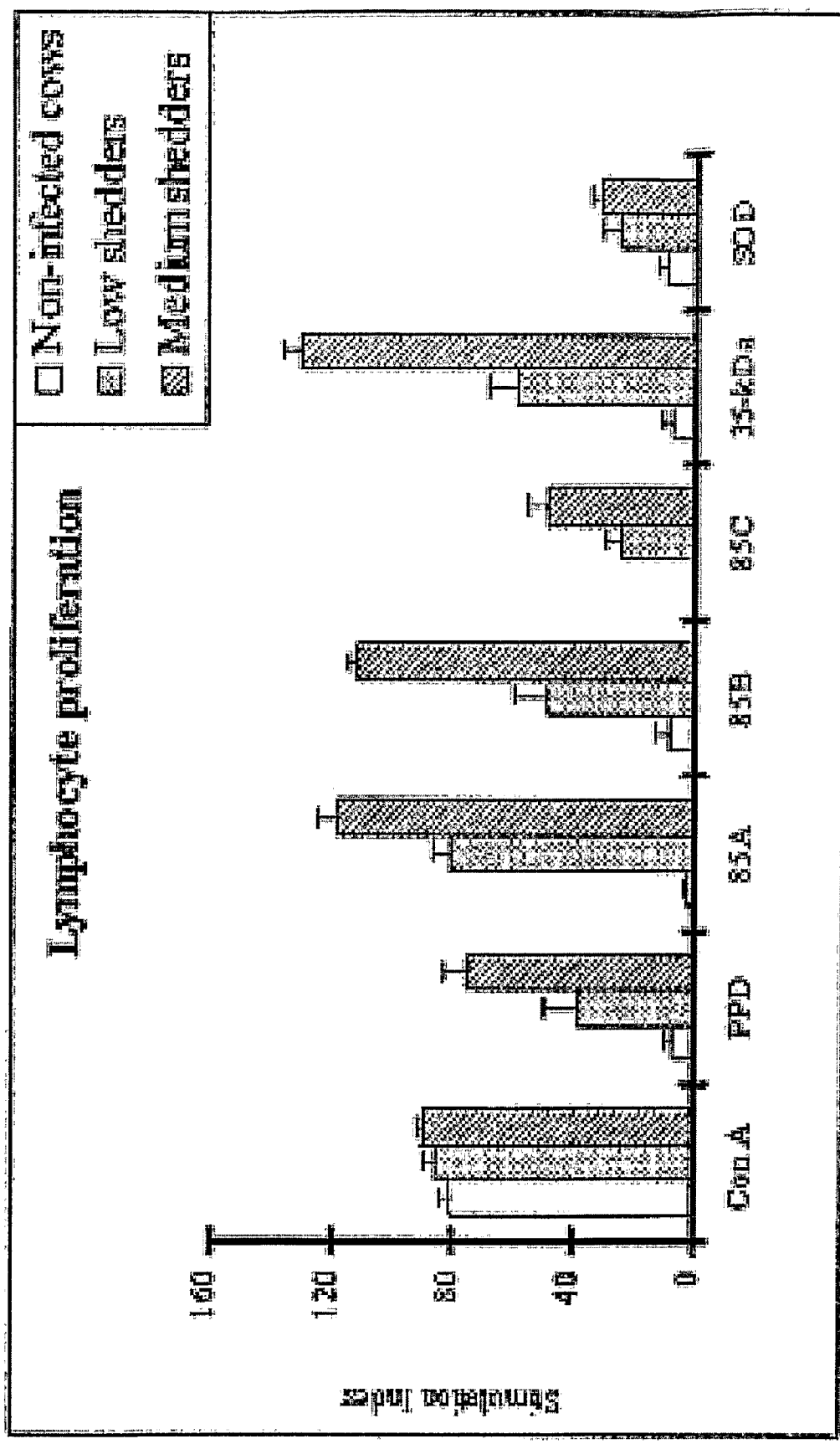
FIG. 1 is a graphical representation of data from analysis of proliferative responses of peripheral blood mononuclear cells from infected and healthy control cows stimulated in vitro with 5 MPT recombinant proteins. The results are expressed as a stimulation index and the error bars represent standard deviation from the mean. No significant proliferation was noted to any antigen by PBMCS from non-infected cows ($P>0.05$). 85A and the 35-kDa protein showed most proliferative activity in low and medium shedders, respectively.

As demonstrated in FIG. 1, proliferative activities of bovine PBMCs from medium shedder cows were higher than other groups in response to all recombinant proteins and two positive controls ($P<0.05$) although there was variation among individual cows. PBMCs from medium shedder cows treated with 85A, 85B and the 35-kDa protein antigens demonstrated a stimulation index (SI) significantly higher ($P<0.005$) than that of PBMCs treated with other recombinant antigens. In addition, proliferative responses to the 35 kDa protein in low shedders were even greater than those of medium shedders in response to 85C and SOD (FIG. 1). Thus, this Example indicates that the 85A, 85B and the 35-kDa protein antigens may be important in affecting lymphocyte proliferation is animals previously exposed to MPT.

Example 2

This Example demonstrates the effects of recombinant antigens on IFN-γ production. To analyze IFN-γ production, IFN-γ levels were measured in culture supernatants using a commercial kit specific for bovine IFN-γ following the manufacturer's instructions (Biosource Int. Camarillo, Calif.). The plates were read at 450 nm in a Bio-Tek 312E ELISA reader (BioTEK Instruments, Inc, Winooski, Vt. 05404-0998), using any reference filter from 630 nm to 750 nm. The results were calculated based on comparison of negative and positive control optional density (O.D). Results were determined as either negative (<OD of positive control) or positive (>OD of positive control) relative to the cut-off value according to the manufacturer's instructions.

IFN-γ production after stimulation with the five recombinant antigens or two positive controls was measured in PBMCs from infected and uninfected control cows. The results are presented in FIG. 2 as corrected OD values (OD of antigen stimulated minus OD of control) representing the elevation of IFN-γ production by the various antigens.

Figure 2:
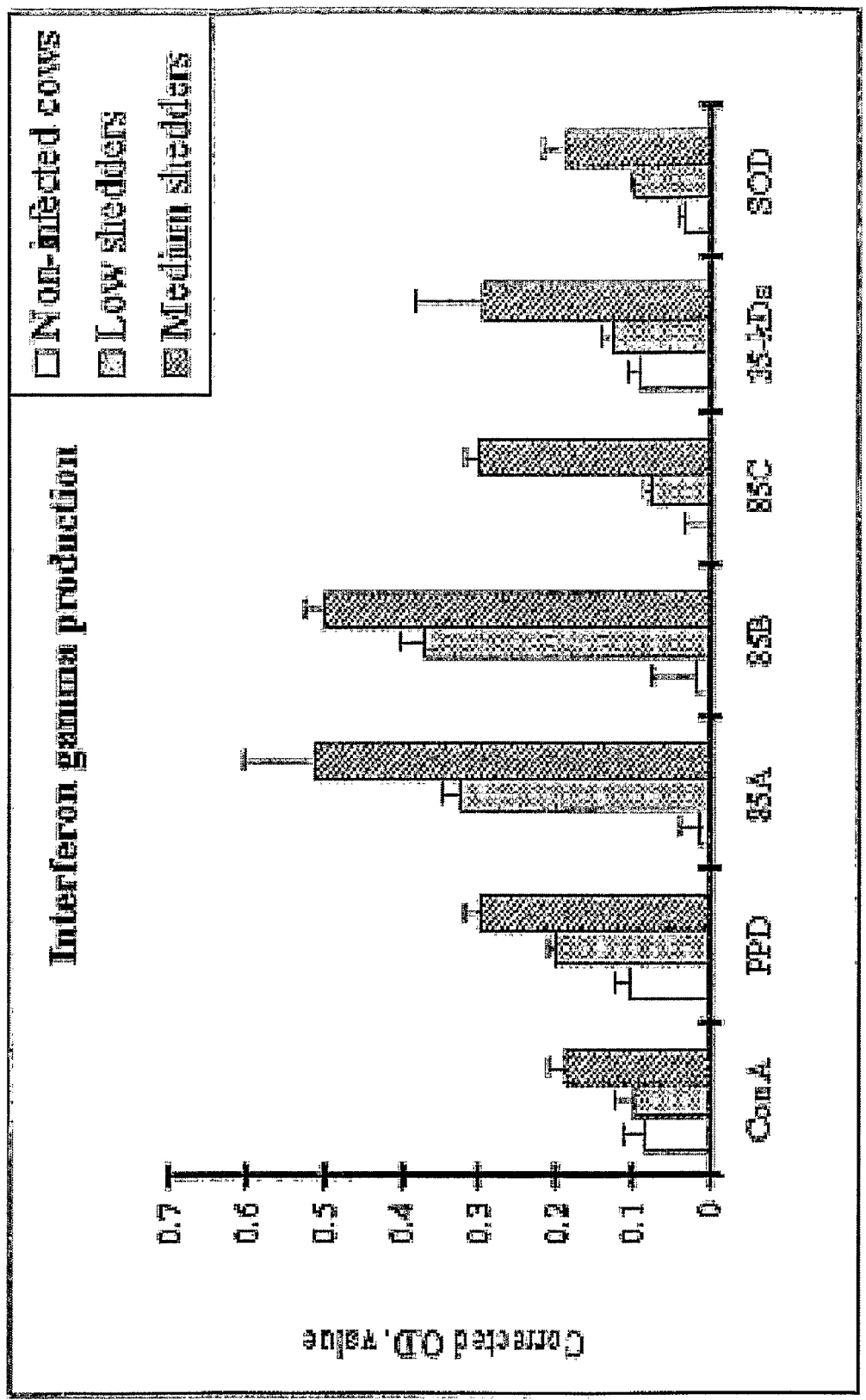
FIG. 2. is a graphical representation of data from analysis of interferon-$\gamma$ production in response to individual antigens in related to MPT shedding levels. The results are given as O.D. values in stimulated wells—O.D. values in control (naturally produced IFN-$\gamma$) wells. Error bars represent standard deviations from the means. 85A and 85B were most inducible antigens to produce IFN-$\gamma$ in bovine peripheral blood mononuclear cells from both shedders.

As can be seen from FIG. 2, all recombinant antigens tested induced significant release of IFN-γ in cultures of bovine PBMCs from infected cattle compared to uninfected controls ($P<0.05$), and IFN-g levels were consistently higher in medium shedders than in low shedders ($P<0.05$). The recombinant antigens 85A and 85B induced significantly higher levels of IFN-γ in the low shedders than the other recombinant antigens tested and as compared to the two positive controls (P<0.05). Thus, this Example indicates the recombinant antigens 85A and 85B may be important in stimulating a cell-mediated response against MPT.

Example 3

This Example provides a comparison of antibodies in sera isolated from non-infected and infected cows which recognize the recombinant antigens of the invention.

Enzyme-linked immunosorbent assays (ELISA) were performed to evaluate the seroreactivity of the recombinant antigens following steps as previously described (Shin, et al., (2004) J. Vet. Sci. 5:111-117). Briefly, an indirect ELISA was optimized using 2.5, 5 or 10 µg/mL of each antigen and 1:100 diluted serum by checkerboard titration. Flat-bottomed 96-well plates (Maxisorp, Nunc, Denmark) were coated with 100 µL of each antigen in carbonate-bicarbonate buffer (14.2 mM $Na_2CO_3$, 34.9 mM $NaHCO_3$, 3.1 mM $NaN_3$, pH 9.5) at 4° C. overnight, followed by washing three times with PBS containing 0.05% Tween 20 (PBST, washing buffer) using a microwell plate washer Bio-Tek ELx405 (BioTEK Instruments, Inc, Winooski, Vt.). Uncoated sites in the wells were blocked with 5% skim milk in PBST at 37° C. for 1 h. The plates were washed twice with PBST and 100 µL of optimally diluted (1:25,000) conjugated anti-bovine IgG-HRP (Sigma) was added to all wells and incubated at 37° C. for 1 h. The plates were washed three times in PBST and 200 µL of 2-2'-Azino-Bis-Thiazoline-6-Sulfonic acid (Sigma) was added to each well. The plates were incubated at 37° C. in the dark. After 30 min incubation, stop solution (1M HCl) was added and the plates were read 3 times at 405 nm at 2-minute intervals in a Bio-Tek 312 ELISA reader (BioTEK Instruments, Inc, Winooski, Vt. 05404-0998). Positive and negative sera and antigen and antibody controls were included in each plate.

Figure 3:
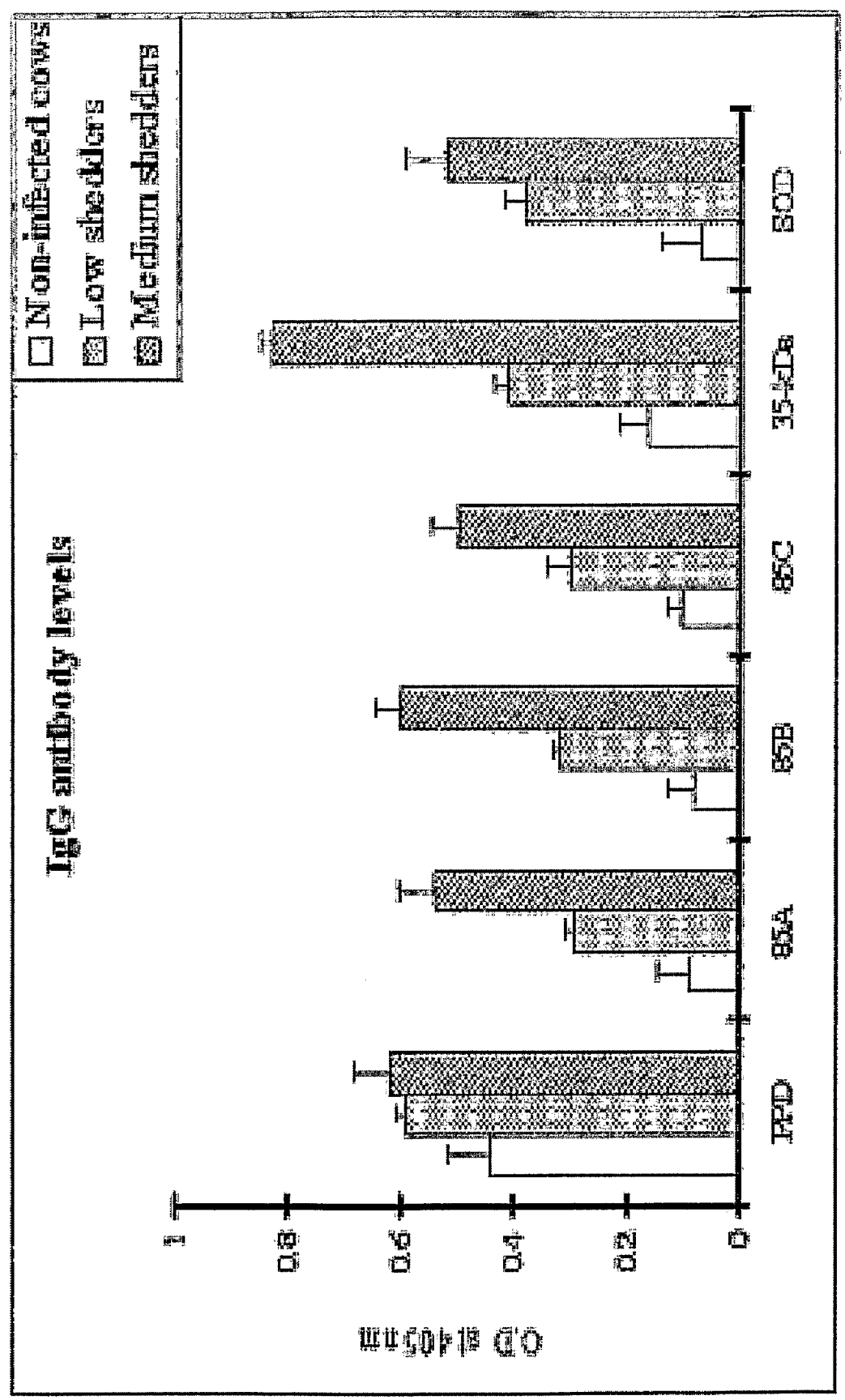
FIG. 3. is a graphical representation of data from analysis of antibody responses to individual antigens in relation to MPT shedding levels. Bars represent the means O.D. values at 405 nm. Error bars represent standard deviations from the means. All recombinant antigens showed increases of antibody responses according to shedding levels and antibody responses to the 35-kDa protein were positively separated between non-infected healthy cows and both shedders ($P<0.01$).

The results from measuring levels of IgG antibodies to the recombinant antigens in sera from both shedder groups and healthy controls are depicted in FIG. 3. Although there was a wide variation in antibody content in sera from individual cows, the mean IgG antibody responses against all recombinant antigens increased significantly in both the low and medium shedder groups. No significant differences were observed among the mean levels of antibody of the low shedder group to any of the antigens tested (FIG. 3). Strikingly, antibody responses to the 35-kDa protein were significantly higher in the medium shedder group than those to the other antigens (P<0.05), which may be important because the 35-kDa protein is also effective at stimulating lymphocyte proliferation, and thus may stimulate both cell-mediated and humoral immune responses.

Example 4

This Example demonstrates changes in lymphocyte subset distribution in PBMCs obtained from non-infected, low shedder and medium shedder cows in response to stimulation with the recombinant antigens.

To perform this analysis, a single-color flow cytometric analysis was performed with monoclonal antibodies against bovine lymphocyte markers (Table 2). Briefly, cells were washed three times in FACS buffer, incubated with the first

TABLE 2

| Monoclonal antibody | Isotype | Antigen identified | Ab Reference |
|---|---|---|---|
| IL-A11 | IgG2a | CD4 | (Brodersen, et al., 1998. Vet. Immunol. Immunopathol. 64: 1-13) |
| CACT80C | IgG1 | CD8α | (Davis, et al. 1989. Am. Fish. Soc. Symp. 7: 521-540.) |
| MM1A | IgG1 | CD3 | (Rhodes, et al. 2001. J. Immunol. 166: 5604-5610) |
| BAQ15A | IgM | CD21 B cells | (Mukwedeya, et al. 1993. Vet Immunol Immunopathol 39: 177-186) |
| CACT116A | IgG1 | CD25 (IL-2Ra) | (Naessens et al. 1992. Immunology 76: 305-309.) |
| CACT63A | IgG1 | γδ T cells | (Davis, et al. 1996. Vet. Immunol. Immunopathol. 52: 301-311) | antibody (Table 1) for 30 min at 4 C, washed three times, subsequently incubated with a fluorescein isothiocyanate-labeled horse anti-mouse immunoglobulin antibody (Vector) for 30 min at 4 C, washed twice, and collected in 200 µl of FACS fixer buffer prior to analysis. Analysis was done on a flow cytometer (FACSCalibur; Becton Dickson). A forward-scatter-side-scatter live gate was used to measure 5,000 to 10,000 lymphocytes per sample. Based on the florescence data of the lymphocytes, the results were expressed as the percentage of cells with positive staining relative to a sample stained with an irrelevant isotype control antibody.

As depicted in FIGS. 4A-4D, antigen-stimulated T cell and/or B cell subsets were examined by single color flow cytometry for differences in the percentage of $CD4^+$, $CD8^+$, $CD3^+$ ($CD3^+$ is depicted in FIG. 5), $CD21^+$ and $CD25^+$ lymphocyte subsets, as well as $γδ^+$ T cells in PBMC cultures from both shedder groups and healthy controls after stimulation with each recombinant antigen (FIGS. 4 and 5). All lymphocyte subsets investigated in this study increased but, depending on bacterial shedding levels, there were slight differences (P<0.05) between non-infected cattle and low shedders according to recombinant antigens.

CD3 is a pan T-cell marker that is expressed by $CD4^+$ and $CD8^+$ cells as well as $γσ^+$ T cells. The proportion of $CD25^+$ T cells increased in culture regardless of the recombinant antigen used (P<0.05) (FIG. 4C). These results suggest that all antigens used in this study are able to stimulate sensitized T cells.

While all recombinant antigens tested increased the proportion of $CD4^+$ cells in cultures of bovine PBMCs from infected cattle compared to uninfected controls (P<0.05), 85A and 85B increased the proportion of $CD4^+$ T cells to significantly higher levels than 85C, the 35-kDa protein, and SOD (P<0.05) (FIG. 4A). The proportion of $CD4^+$ T cells was also greater in cultures treated with 85A and 85B among PBMCs from medium shedders than from low shedders (P<0.05) (FIG. 4A). Further, 85A and 85B did not increase $CD4^+$ T cells in noninfected cattle. While not intending to be bound by any particular theory, these results may indicate that 85A and 85B antigens induce $CD4^+$ T cells specifically sensitized by MTP and provide protective immunity against MTP infection by maintaining circulating $CD4^+$ T-cell populations in the early infectious phase, i.e., at the time mucosal colonization by MPT is first occurring.

In contrast to the increase of $CD4^+$ cells induced by all the antigens relative to uninfected controls, a significant increase in the proportion of $CD8^+$ T cells was found only in cultures treated with 85A, 85B, and 85C and the proportion of $CD8^+$ cells was also greater in cultures treated with 85A and 85B among PBMCs from medium shedders than from low shedders ($P<0.05$) (FIG. 4B). Thus, these antigens may preferentially stimulate cell mediated responses.

Only SOD was able to significantly increase the proportion of $\gamma\sigma^+$ T cells in the cultures of medium shedders ($P<0.05$) (FIG. 4D). However, SOD stimulated lymphocytes to a lesser degree than the other antigens tested, except for $\gamma\sigma^+$ T lymphocytes, as the number of $\gamma\sigma^+$ T cells was significantly higher in PBMC cultures treated with SOD in noninfected cattle, as well as in both shedder groups (FIG. 4D). Thus, SOD may preferentially stimulate $\gamma\sigma^+$ T lymphocytes compared to the other antigens. Further, because $\gamma\sigma^+$ T cells are numerous in mucosal tissues, which is the point of entry for mycobacterial pathogens, the SOD antigen may be important in the earlier stages of infection via its preferential stimulation of $\gamma\sigma^+$ T cells.

All recombinant antigens tested significantly increased the proportion of $CD21^+$ B cells in cultures of bovine PBMCs from both low and medium shedders compared to uninfected controls (P 0.05) (FIG. 6). Interestingly, the proportion of $CD21^+$ B cells was significantly higher in cultures of bovine PBMCs from medium shedders than that of the other recombinant antigens tested ($P<0.05$).

Example 5

This Example provides a comparison of stimulation of cytokine mRNA production in bovine PBMC's after stimulation with recombinant antigens.

For preparation of RNA and DNase I treatment of cells, PBMC cell pellets were obtained and washed twice in 50 mL phosphate buffered saline (PBS), pelleted and $5 \times 10^6$ cells were lysed with 350 µL lysis buffer according to the manufacturer's recommendations (RNeasy mini kit, Qiagen, Calif.) and kept at −80 C until RNA extraction and complementary DNA (cDNA) synthesis. Total RNA (tRNA) was extracted from lysed cells or PMBCs using the RNeasy mini kit (Qiagen). The extracted tRNA was treated with 10 U/µl of RNase-free DNase I at 37 C for 10 min followed by heat inactivation at 95 C for 5 min and then chilled on ice.

For cDNA synthesis, reverse transcription (RT) was performed in a 20 µL final volume containing 1.6 µL total RNA, 200 U Superscript II RT (GibcoBRL), 50 mM Tris-Hcl (pH 8.3), 75 mM KCl, 3 mM MgCl2, 0.01 M DTT, and 0.5 mM dNTPs. The reaction mix was subjected to 42 C for 50 min and inactivated at 70 C for 15 min. The cDNA was analyzed immediately or stored at −20 C until use.

To perform real-time quantitative (RT-PCR), approximately 1 to 5 µg of total RNA from each treatment group was reverse transcribed by using Superscript reverse transcriptase, Random Hexamers, and reverse transcriptase reagents (Gibco BRL). Real-time primers and probes were designed by Primer Express software (Applied Biosystems) using the sequences for bovine GAPDH, cytokines and growth factors obtained from Genbank. The internal probes were labeled with the florescent reporter dye 5-carboxyfloroscein (FAM) on the 5' end and the quencher dye N',N',N', N',N'-tetramethyl-6-carboxyrhodamine (TAMRA) on the 3' end. The PCR mixture consisted of 400 nM primers, 80 nM Taqman probe and commercially available PCR Mastermix (TaqMan Universal PCR Mastermix, Applied Biosytems) containing 10 mM Tris-HCl (pH 8.3), 50 mM KCl, 5 mM $MgCl_2$, 2.5 mM deoxynucleotide triphosphates, 0.625 U AmpliTaq Gold DNA polymerase per reaction, 0.25 U AmpErasw UNG per reaction and 10 µl of the diluted cDNA sample in a final volume of 25 µl. The samples were placed in 96-well plates and amplified in an automated flurometer (ABI Prism 7700 Sequence Detection System, Applied Biosystems). Amplicon conditions were 2 min at 50 C, 10 min at 95 C, followed by 40 cycles at 95 C for 15 s and 60 C for I min. Final quantitation was done using the comparative cycle threshold ($C_T$) method and is reported as relative transcription or the n-fold difference relative to a calibrator cDNA.

As can be seen from FIG. 7, all recombinant antigens stimulated high levels of IL-2 mRNA from PBMCs of medium shedders, with the antigen 85 complex having a greater effect than either the 35-kDa protein or SOD ($P<0.05$) (FIG. 7). 85A also induced a high level of IFN-γ, IL-12p40, and TNF-α mRNA (FIGS. 8A, B, and C, respectively) in medium shedders ($P<0.05$). Strikingly, PBMCs stimulated with the 35-kDa protein antigen highly expressed IL-4 mRNA in both low and medium shedders ($P<0.05$) (FIG. 9). This induction of IL-4 mRNA by the 35-kDa protein significantly increased depending on shedding levels ($P<0.001$). In contrast, no significant differences were observed among the other antigens ($P>0.05$). These studies are in agreement with the results presented in Example 3 which indicate immune responses to the 35-kDa protein may be more important in the later stage of disease since flow cytometric analysis showed that the 35-kDa protein strongly induced proliferation of B lymphocytes, especially in medium shedders (FIG. 3). Thus, this Example demonstrates that all of the recombinant antigens tested may stimulate a cell-mediated immunological response.

Example 6

This Example demonstrates the effect of vaccinating mice with DNA polynucleotides encoding MPT antigens and subsequent challenge with MPT.

For demonstrating of the effect of the DNA constructs, specific-pathogen-free C57/BL6 female mice were obtained from the Harlan Sprague Dawley Inc (Indianapolis, Ind.). The mice were ~8 weeks old at the time of vaccination. There were five groups of mice and each vaccine group consists of 25 animals during this experiment. The animals were fed commercial mouse chow and water ad libitum, and maintained on a 12/12-hour light/dark cycle.

The commercially available eukaryotic expression plasmid pVR1020 (Vical, Inc., San Diego, Calif.) was used for the DNA vaccine. This plasmid contains an immediate-early cytomegalovirus promoter to ensure efficient expression in a eukaryotic host as well as the human tissue plasminogen activator (hTPA) secretion signal to facilitate secretion of the target antigen from the eukaryotic cell (Brandt, et al. 2000. Infect. Immun. 68:791-795). DNA encoding MPT 85A, 85B, 85C, SOD, 35 kDa, 35 kDa(li), MptC, MptD, and ESAT-6 like genes was amplified by polymerase chain reaction from MPT genomic DNA using the gene specific primers listed in Table 1. Briefly, the primers used for amplification of MPT 85A, 85B and 85C coding sequences each included a BamHI site. One primer for amplification of SOD, MptC, MptD, 35 kDa, and ESAT6-like coding sequences included a BamHI site while the other included a BglII site. The amplification products were digested using the indicated restriction enzymes and cloned into the commercially available pCR2.1 TOPO cloning vector (Invitrogen, CA) using standard techniques. The MPT genes were then subcloned downstream of the human tissue plasminogen activator (hTPA) secretion signal in the pVR1020 plasmid (Vical, Inc., San Diego, Calif.) using standard techniques and essentially as previously described (Dheenadhayalan et al., (2002) DNA Seq.

13:287-294; Shin et al., (2004) J. Vet. Sci. 5:111-117) (Skeiky et al., (1998) J. Immunol. 161:6171-6179). These recombinant constructs were transfected into HEK-293 (human embryonic kidney) cells with using Lipofectamin™ 2000 transfection reagent (Invitrogen, CA) and the expression of the antigen genes was confirmed at the transcription level using RT-PCR.

For immunization and MPT challenge, mice were divided into five different groups (Table 3). The animals were administered with 50 µg of each DNA in 50 µl

TABLE 3

| | Groups | | | |
|---|---|---|---|---|
| 1 | 2 | 3 | 4 | 5 |
| DNA Vaccine 85A, 85B 85C, 35 kDa and SOD | Group1 + IL-12 | MptC, MptD ESAT6like and 35 kDa(Li) | Group3 + IL-12 | Vector Control (pVR1020) |

PBS per dose via intramuscular injection. Mice were immunized three times at 3-week intervals. IL-12 genes were additionally injected as indicated in Table 3. Three weeks after the second boosters, the animals were challenged by intraperitoneal injection of $10^9$ CFU units of (MPT). Six animals in each group were sacrificed at $4^{th}$, $8^{th}$, $12^{th}$ and $16^{th}$ week after challenge and the recovery of bacteria from organs (liver, spleen, mesenteric lymph node, lung) was enumerated on Herald's EggYolk (HEY) slant agar supplemented with Mycobactin J and antibiotics as previously described (Kamath, et al. Infect. Immun. 67:1702-1707). After challenge, feces were also collected every week from mouse cages and cultured using the same agar. Tissues including liver, spleen, lung, intestine and mesenteric lymph node were fixed by immersion in 10% buffered formalin and processed for histopathological examination using standard histotechnology techniques. The presence of MPT (acid-fast bacteria) in the liver and spleen of each mouse was assessed by Ziehl-Neelsen staining.

FIG. 10 shows the decreased mycobacterial burden in the livers and spleens of vaccinated mice relative to controls at 4, 8 and 12 weeks post-challenge and demonstrates an approximately 90% reduction (1 log 10) in the bacterial burden in the spleens and livers for mice vaccinated with the MPT DNA vaccine cocktail compared to non-immunized controls. The relative liver and spleen histopathology data at 4, 8 and 12 weeks post-challenge paralleled the bacterial growth results. Substantive differences were seen in liver and spleen tissues taken from animals immunized with the plasmid cocktail compared to nonimmunized mice (FIG. 11). MPT infected nonvaccinated controls had numerous randomly dispersed granulomas with central epithelioid macrophages surrounded by small lymphocytes. Ziehl-Neelsen staining revealed numerous acid-fast bacilli were seen (FIG. 12A and inset). In contrast, the infection was much less severe in the mice vaccinated with the MPT DNA vaccine cocktail (FIG. 12B).

Thus, this Example demonstrates that administration with a DNA expression vectors encoding at least five MPT antigens can provide significant protection from MPT infection.

I claim:

1. A method of stimulating an immune response against *Mycobacterium Avium* Subspecies *Paratuberculosis* (MPT) in a ruminant comprising administering an amount of a cocktail composition comprising at least five immunogenic components, wherein the immunogenic components are isolated polynucleotide sequences encoding full length MPT protein antigens 85A, 85B, 85C, MPT 35 kDa protein, and superoxide dismutase (SOD).

2. The method of claim 1, wherein the ruminant is a bovine, a sheep, a goat, a deer or an elk.

3. The method of claim 2, wherein the ruminant is a bovine.

4. The method of claim 1, wherein the ruminant is not infected with MPT.

5. The method of claim 1, wherein the ruminant is infected with MPT.

6. The method of claim 2, wherein the bovine has Johne's Disease.

7. The method of claim 1, wherein the composition further comprises a pharmaceutically acceptable carrier.

8. The method of claim 1, wherein the ruminant is pregnant.

9. The method of claim 7, wherein the composition further comprises an adjuvant.

* * * * *